US007223850B1

(12) United States Patent
Luo et al.

(10) Patent No.: US 7,223,850 B1
(45) Date of Patent: May 29, 2007

(54) APOPTOSIS PROTEINS

(75) Inventors: Ying Luo, Los Altos, CA (US); Betty Huang, San Leandro, CA (US); Mary Shen, Newark, CA (US); Pei Wen Yu, Cupertino, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 183 days.

(21) Appl. No.: 09/762,491

(22) PCT Filed: Aug. 6, 1999

(86) PCT No.: PCT/US99/17776

§ 371 (c)(1),
(2), (4) Date: May 9, 2001

(87) PCT Pub. No.: WO00/07545

PCT Pub. Date: Feb. 17, 2000

Related U.S. Application Data

(60) Provisional application No. 60/099,486, filed on Sep. 8, 1998, provisional application No. 60/095,590, filed on Aug. 6, 1998, provisional application No. 60/095,587, filed on Aug. 6, 1998.

(51) Int. Cl.
*C12N 15/11* (2006.01)
*C07K 14/00* (2006.01)
(52) U.S. Cl. .................. 536/23.1; 435/320.1; 435/4; 435/6; 530/350
(58) Field of Classification Search .............. 424/94.1; 435/183, 325, 6; 530/350; 536/23.1, 23.5, 536/24.3, 24.31, 24.33
See application file for complete search history.

(56) References Cited

U.S. PATENT DOCUMENTS 6,096,539 A * 8/2000 Gomes et al. ............... 435/325
6,267,956 B1 * 7/2001 Gomes et al. ............... 424/94.1

FOREIGN PATENT DOCUMENTS

WO    WO 96/36730 A1    11/1996
WO    WO 97/15586 A1    5/1997

OTHER PUBLICATIONS

Wang, J. et al. 2000 J. Biol. Chem. 275 (1): 507-513.*
Cao, et al., "Human Gastric Adenocarcinoma Cathepsin B: Isolation and Sequencing of Full-Length cDNAs and Polymorphisms of the Gene", *Gene* (1994), vol. 139, pp. 163-169.
Chan, et al., "Nucleotide and Predicted Amino Acid Sequences of Cloned Human and Mouse Preprocathespin B cDNAs", *Proceedings of the National Academy of Sciences USA* (1986), vol. 83, pp. 7721-7725.
Cohen, Gerald, M., "Caspases: the Executioners of Apoptosis", *Biochemistry Journal* (1997), vol. 326, pp. 1-16.

Del Peso, L., et al., "Interleukin-3-Induced Phosphorylation of BAD Through the Protein Kinase Akt", *Science* (1997), vol. 278, pp. 687-689.
Fong, D., et al., Isolation of a cDNA Clone for the Human Lysosomal Proteinase Cathepsin B, *Proceedings of the National Academy of Sciences USA* (1986), vol. 83, pp. 2909-2913.
Moin, K., et al., "Human Tumour Cathepsin B—Comparison with Normal Liver Cathepsin B", *Biochemical Journal* (1992), vol. 285, pp. 427-434.
Nägler, D. et al., "Full-Length cDNA of Human Cathespin F Predicts the Presence of a Cystatin Domain at the N-terminus of the Cysteine Protease Zymogen", *Biochemical and Biophysical Research Communications* (1999) vol. 257, pp. 313-318.
Ritonja, A., et al., "Amino Acid Sequence of Human Liver Cathespin B", *Federation of European Biochemical Societies*, (1985), vol. 181, No. 1, pp. 169-172.
Santamaria, I., et al., "Molecular Cloning and Structural and Functional Characterization of Human Cathespin F, a New Cysteine Proteinase of the Papain Family with a Long Propeptide Domain", *Journal of Biological Chemistry* (1999), vol. 274, No. 20, pp. 13800-13809.
Sun, X., et al., *The Journal of Biological Chemistry* (1999), vol. 274, No. 24, pp. 16871-16875.
Takahashi, R., et al., A Single BIR Domain of XIAP Sufficient for Inhibiting Caspases, *The Journal of Biological Chemistry* (1998), vol. 273, No. 14, pp. 7787-7790.
Thome, M., et al., "Syk and ZAP-70 Mediate Recruitment of p56$^{lck}$/CD4 to the Activated T Cell Receptor CD3/ζ Complex", *Journal of Experimental Medicine* (1995), vol. 181, pp. 1997-2006.
Wang, B., et al., "Human Cathespin F—Molecular Cloning, Functional Expression, Tissue Localization, and Enzymatic Characterization", *Journal of Biological Chemistry* (1998), vol. 273, No. 48, pp. 32000-32008.

(Continued)

*Primary Examiner*—Misook Yu
(74) *Attorney, Agent, or Firm*—Townsend and Townsend and Crew LLC

(57) ABSTRACT

The present invention is directed to novel apoptosis polypeptides such as the Apop1, and Apop3 proteins and related molecules which are involved in modulating apoptosis and to nucleic acid molecules encoding those polypeptides. Also provided here are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention. Further provided by the present invention are methods for identifying novel compositions which modulate the biological activity of Apop1, Apop2, and Apop3, and the use of such compositions in diagnosis and treatment of disease.

24 Claims, 8 Drawing Sheets

OTHER PUBLICATIONS

Wex, TH., et al. "Human Cathepsins F and W: A New Subgroup of Cathepsins", *Biochemical and Biophysical Research Communications* (1999), vol. 259, pp. 401-407.
Yu , P., et al., "Identification of RIP3, a RIP-like Kinase That Activates Apoptosis and NFκB", *Current Biology* (1999), vol. 9, pp. 539-542.
Accession No. NM_001908, submitted Aug. 29, 2002.
Accession No. M14221, submitted 1986.
Accession No. P07858, submitted Jul. 1, 1989.
Accession No. NP_001899, submitted 1986.
Accession No. AF071748, submitted Jun. 9, 1998.
Accession No. NM_003793, submitted Oct. 15, 1999.
Accession No. AF088886, submitted May 3, 1999.
Accession No. AJ007331, submitted Jun. 20, 1998.
Accession No. AF132894, submitted Mar. 3, 1999.
Accession No. AA338898, submitted Apr. 21, 1997.
Accession No. H39591, submitted Jul. 31, 1995.
Accession No. AA378321, submitted Apr. 21, 1997.
Accession No. AA227673, submitted Nov. 27, 1996.
Accession No. N99896, submitted Apr. 15, 1996.
Accession No. AI394293, submitted Feb. 4, 1999.

* cited by examiner

| | |
|---|---|
| 1 | CACAGACAGGCTCTTAACTGTTTATATCACTCACTTGGGAAAGTGTCTCAAGCTGTTCTA |
| 61 | CAAATCCATGCAAAGGCCGTTTAAAAATAGCAGCGAAGGTCCTGGACTCGGTCTCGTCCA |
| 121 | GCACAGCCCCTTGGCTCTCTCTCTGGGCTCTGGCCGCCTGGCCCCGGGGACCCACACGA |
| 181 | GGTCATGGCGTGCTTCGGGCAGGGGGGCGGGGATCCCATAGACACCTCAGCTCCTTAAGA |
| 241 | GTTCTCCGCCTGGGCCAGGACGAGCATGGGGGTCCCCACTGATGCCCGAGACAGTGCCCC |
| 301 | TGTGTGTGTGAGCCCTCGACCCACATAACAGAGAGGTGTCCTGATGCCCTCTGTCCTCTC |
| 361 | CAGGTGGATCTAGGATCCGGCTTCCAAC<u>ATG</u>TGGCAGCTCTGGGCCTCCCTCTGCTGCCT |
| 421 | GCTGGTGTTGGCCAATGCCCGGAGCAGGCCCTCTTTCCATCCCGTGTCGGATGAGCTGGT |
| 481 | CAACTATGTCAACAAACGGAATACCACGTGGCAGGCCGGGCACAACTTCTACAACGTGGA |
| 541 | CATGAGCTACTTGAAGAGGCTATGTGGTACCTTCCTGGGTGGGCCCAAGCCACCCCAGAG |
| 601 | AGTTATGTTTACCGAGGACCTGAAGCTGCCTGCAAGCTTCGATGCACGGGAACAATGGCC |
| 661 | ACAGTGTCCCACCATCAAAGAGATCAGAGACCAGGGCTCCTGTGGCTCCTGCTGGGTAAG |
| 721 | GCCCTGCTGGCTGGTGGGGAAGCGCTGGAGAGAAAGTGGGAGCAACACTGGAGAGTCTTG |
| 781 | GGGGATTCGGGGTGGGGACAACTCTGACAAGGCAAGTTATAGAAACTTTCTGAGTCCCAG |
| 781 | TTTCCATCAGTACAAAAATCACAATCCCTCTGGCCATGAA<u>TGA</u>TGGCGAGGATTAGGTGG |
| 841 | AGTGGCGGGCAGAGCATCCAGCAGATTGCAAGTCCACGTGTACAGGTGGCGAAGCAGCTC |
| 901 | CCTTTCCCTGACATGCTGGCCCGTCCGCAAATACCAGGAGCTCTCACTGCTACTCTGCTT |
| 961 | CAAGAAAGCATCCCTTTAGTGTCAGTGAGCTGTCTTAATTTTGTCATTTAATTGTGGTAA |
| 1021 | AATACACGTAACAGAAATGTAATAATCTTAGCAATCTTCTTTTGTTTTCTTTTTCTTTTT |
| 1081 | TTTTTTTTTTTTTTT |

FIGURE 1

```
  1 MWQLWASLCCLLVLANARSRPSFHPVSDELVNYVNKRNTTWQAGHNFYNVDMSYLKRLCG
 61 TFLGGPKPPQRVMFTEDLKLPASFDAREQWPQCPTIKEIRDQGSCGSCWVRPCWLVGKRW
121 RESGSNTGESWGIRGGDNSDKASYRNFLSPSFHQYKNHNPSGHE
```

FIGURE 2

```
   1 TCCAAGTCCTGGATGAGCTCGGAAGACACGTGCTGCTGCGGAAGGACTGTGGCCCAGTGG
  61 ACACCAAGGTTCCAGGTGCTGGGGAGCCCAAGTCAGCCTTCACTCAGGGCTCAGCCATGA
 121 TTTCTTCTCTGTCCCAAAACCATCCAGACAACAGAAACGAGACTTTCAGCTCAGTCATTT
 181 CCCTGTTGAATGAGGATCCCCTGTCCCAGGACTTGCCTGTGAAGATGGCTTCAATCTTCA
 241 AGAACTTTGTCATTACCTATAACCGGACATATGAGTCAAAGGAAGAAGCCCGGTGGCGCC
 301 TGTCCGTCTTTGTCAATAACATGGTGCGAGCACAGAAGATCCAGGCCCTGGACCGTGGCA
 361 CAGCTCAGTATGGAGTCACCAAGTTCAGTGATCTCACAGAGGAGGAGTTCCGCACTATCT
 421 ACCTGAATACTCTCCTGAGGAAAGAGCCTGGCAACAAGATGAAGCAAGCCAAGTCTGTGG
 481 GTGACCTCGCCCCACCTGAATGGGACTGGAGGAGTAAGGGGCTGTCACAAAAGTCAAAG
 541 ACCAGGGCATGTGTGGCTCCTGCTGGGCCTTCTCAGTCACAGGCAATGTGGAGGGCCAGT
 601 GGTTTCTCAACCAGGGGACCCTGCTCTCCCTCTCTGAACAGGAGCTCTTGGACTGTGACA
 661 AGATGGACAAGGCCTGCATGGGCGGCTTGCCCTCCAATGCCTACTCGGCCATAAAGAATT
 721 TGGGAGGGCTGGAGACAGAGGATGACTACAGCTACCAGGGTCACATGCAGTCCTGCAACT
 781 TCTCAGCAGAGAAGGCCAAGGTCTACATCAATGACTCCGTGGAGCTGAGCCAGAACGAGC
 841 AGAAGCTGGCAGCCTGGCTGGCCAAGAGAGGCCCAATCTCCGTGGCCATCAATGCCTTTG
 901 GCATGCAGTTTTACCGCCACGGGATCTCCCGCCCTCTCCGGCCCCTCTGCAGCCCTTGGC
 961 TCATTGACCATGCGGTGTTGCTTGTGGGCTACGGCAACCGCTCTGACGTTCCCTTTTGGG
1021 CCATCAAGAACAGCTGGGGCACTGACTGGGGTGAGAAGGGTTACTACTACTTGCATCGCG
1081 GGTCCGGGGCCTGTGGCGTGAACACCATGGCCAGCTCGGCGGTGGTGGACTGAAGAGGGG
1141 CCCCCAGCTCGGGACCTGGTGCTGATCAGAGTGGCTGCTGCCCCAGCCTGACATGTGTCC
1201 AGGCCCCTCCCCGGGAGGTACAGCTGGCAGAGGGAAAGGCACTGGGTACCTCAGGGTGAG
1261 CAGAGGGCACTGGGCTGGGGCACAGCCCCTGCTT
```

FIGURE 3

```
1    MISSLSQNHPDNRNETFSSVISLLNEDPLSQDLPVKMASIFKNFVITYNRTYESKEEARW
61   RLSVFVNNMVRAQKIQALDRGTAQYGVTKFSDLTEEEFRTIYLNTLLRKEPGNKMKQAKS
121  VGDLAPPEWDWRSKGAVTKVKDQGMCGSCWAFSVTGNVEGQWFLNQGTLLSLSEQELLDC
181  DKMDKACMGGLPSNAYSAIKNLGGLETEDDYSYQGHMQSCNFSAEKAKVYINDSVELSQN
241  EQKLAAWLAKRGPISVAINAFGMQFYRHGISRPLRPLCSPWLIDHAVLLVGYGNRSDVPF
301  WAIKNSWGTDWGEKGYYYLHRGSGACGVNTMASSAVVD
```

FIGURE 4

```
   1 atgtcgtgcg tcaagttatg gcccagcggt gcccccgccc ccttggtgtc catcgaggaa
  61 ctggagaacc aggagctcgt cggcaaagac gggttcggca cagtgttccg ggcgcaacat
 121 aggaagtggg gctacgatgt ggcggtcaag atcgtaaact cgaaggcgat atccagggag
 181 gtcaaggcca tggcaagtct ggataacgaa ttcgtgttgc gcctagaagg ggttatcgag
 241 aaggtgaact gggaccaaga tcccaagccg gctctggtga ctaaattcat ggagaacggc
 301 tccctgtcgg ggctgctgca gtcccagtgc cctcggccct ggccgctcct ttgccgcctg
 361 ctgaaagaag tggtgcttgg gatgttttac ctgcacgacc agaacccggt gctcctgcac
 421 cgggacctca agccatccaa cgtcctgccg gacccagagc tgcacgtcaa gctggcagat
 481 tttggcctgt ccacatttca gggaggctca cagtcaggga cagggtccgg ggagccaggg
 541 ggcacccctgg gctacttggc cccagaactg tttgttaacg taaaccggaa ggcctccaca
 601  gccagtgacg tctacagctt cgggatccta atgtgggcag tgcttgctgg aagagaagtt
 661 gagttgccaa ccgaaccatc actcgtgtac gaagcagtgt gcaacaggca gaaccggcct
 721 tcattggctg agctgcccca agccgggcct gagactcccg gcttagaagg actgaaggag
 781 ctaatgcagc tctgctggag cagtgagccc aaggacagac cctccttcca ggaatgccta
 841 ccaaaaactg atgaagtctt ccagatggtg gagaacaata tgaatgctgc tgtctccacg
 901 gtaaaggatt tcctgtctca gctcaagagc agcaatagga gattttctat cccagagtca
 961 ggccaaggag ggacagaaat ggatggcttt aggagaacca tagaaaacca gcactctcgt
1021 aatgatgtca tggtttctga gtggctaaac aaactgaatc tagaggagcc tcccagctct
1081 gttcctaaaa aatgcccgag ccttaccaag aggagcaggg cacaagagga gcaggttcca
1141 caagcctgga cagcaggcac atcttcagat tcgatggccc aacctcccca gactccagag
1201 acctcaactt tcagaaacca gatgcccagc cctacctcaa ctggaacacc aagtcctgga
1261 ccccgaggga tcaggggggc tgagagacaa ggcatgaact ggtcctgcag gaccccggag
1321 ccaaatccag taacagggcg accgctcgtt aacatataca actgctctgg ggtgcaagtt
1381 ggagacaaca actacttgac tatgcaacag acaactgcct tgcccacatg gggcttggca
1441 ccttcgggca aggggagggg cttgcagcac cccccaccag taggttcgca agaaggccct
1501 aaagatcctg aagcctggag caggccacag ggttggtata atcatagcgg gaaataa
```

FIGURE 5

```
  1 MSCVKLWPSGAPAPLVSIEELENQELVGKDGFGTVFRAQHRKWGYDVAVKIVNSKAISRE
 61 VKAMASLDNEFVLRLEGVIEKVNWDQDPKPALVTKFMENGSLSGLLQSQCPRPWPLLCRL
121 LKEVVLGMFYLHDQNPVLLHRDLKPSNVLPDPELHVKLADFGLSTFQGGSQSGTGSGEPG
181 GTLGYLAPELFVNVNRKASTASDVYSFGILMWAVLAGREVELPTEPSLVYEAVCNRQNRP
241 SLAELPQAGPETPGLEGLKELMQLCWSSEPKDRPSFQECLPKTDEVFQMVENNMNAAVST
301 VKDFLSQLKSSNRRFSIPESGQGGTEMDGFRRTIENQHSRNDVMVSEWLNKLNLEEPPSS
361 VPKKCPSLTKRSRAQEEQVPQAWTAGTSSDSMAQPPQTPETSTFRNQMPSPTSTGTPSPG
421 PRGNQGAERQGMNWSCRTPEPNPVTGRPLVNIYNCSGVQVGDNNYLTMQQTTALPTWGLA
481 PSGKGRGLQHPPPVGSQEGPKDPEAWSRPQGWYNHSGKZ
```

FIGURE 6

| | Binding To RIP |
|---|---|
| Apop3 | ++++ |
| Apop3(1-436) | + |
| Apop3(1-251) | − |
| Apop3(1-196) | − |
| Apop3(K50D) | ++++ |
| Apop3(82-518) | +++ |
| Apop3(287-518) | − |

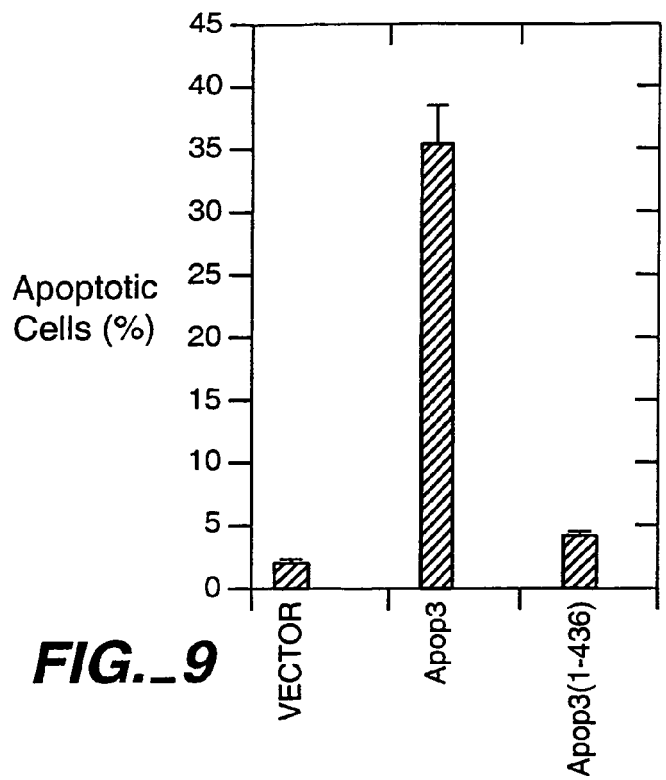
FIG._9
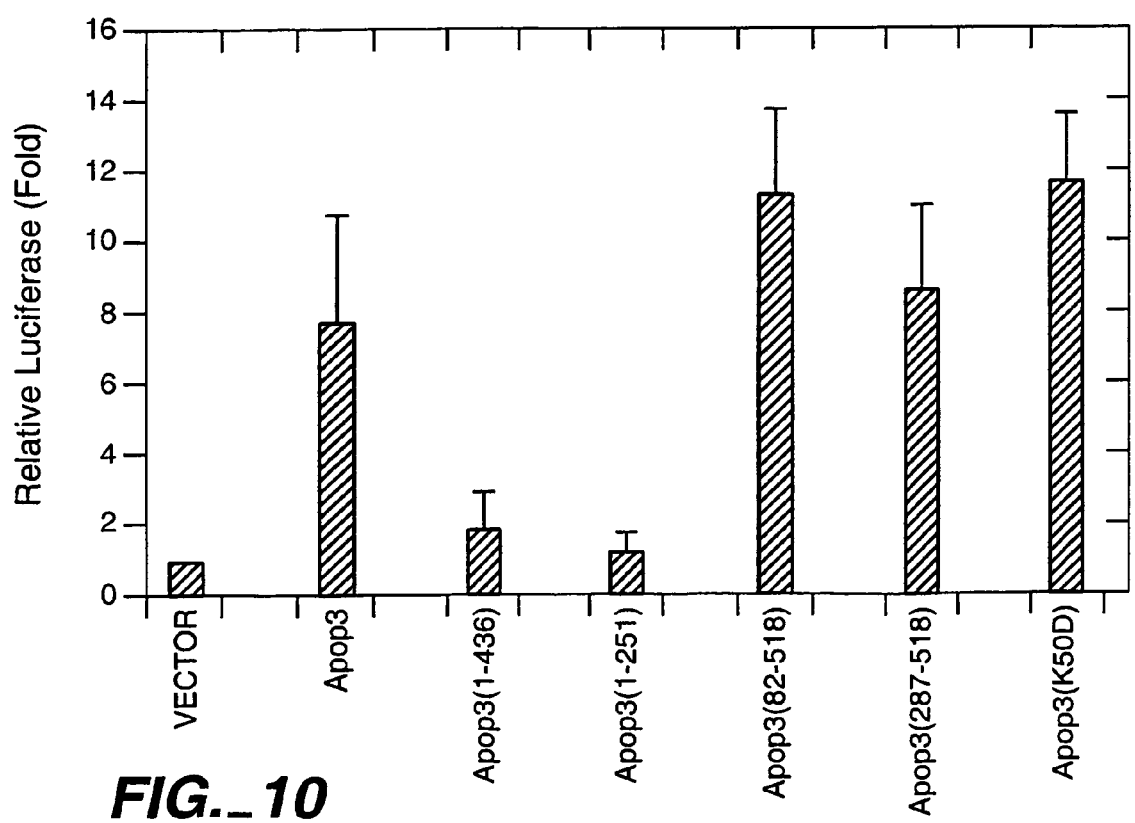
FIG._10

APOPTOSIS PROTEINS

This is a 371 of PCT/US99/17776 filed Aug. 6, 1999, which claims benefit of Ser. No. 60/099,486 filed Sep. 8, 1998, Ser. No. 60/095,590 filed Aug. 6, 1998, and Ser. No. 60/095,587 filed Aug. 6, 1998.

FIELD OF THE INVENTION

The invention relates to novel methods and compositions of apoptosis proteins, collectively termed "Apop proteins", and nucleic acids encoding them. The invention further relates to methods of screening for bioactive agents that bind to and modulate Apop protein function for the diagnosis and treatment of disease.

BACKGROUND OF THE INVENTION

Apoptosis, or programmed cell death, is a highly ordered, genetically controlled process which plays a vital role in both healthy and disease states, including embryogenesis, tissue homeostasis and remodeling, cancer, autoimmune disorders, viral infections, and certain degnerative disorders.

The death domain of TNF receptor-1 (TNFR1) triggers distinct signaling pathways leading to apoptosis and activation of the NF-κB transcription factor through its interaction with the C-terminal death domain of TRADD, a 34 kDA cytoplasmic protein [see Hsu et al., Immunity 4:387-96 (1996)]. TRADD interacts strongly with RIP (receptor-interacting protein; Stanger et al., Cell 81:513-23 (1995), a 74 kDa serine-threonine kinase that with a C-terminal death domain involved in apoptosis; RIP also activates NF-κB. A second RIP protein, RIP2 or RICK [see McCarthy et al., J. Biol. Chem. 273:16968 (1998) and Inohara et al., J. Biol. Chem. 273:12296 (1998)] also contains a death domain and activates NF-κB.

A characteristic feature of apoptosis is activation of a cascade of cytoplasmic proteases that results in the cleavage of selected target proteins. ICE (interleukin 1 beta-converting enzyme) family proteases, also known as caspase proteases, initiate the active phase of apoptosis by degrading specific structural, regulatory, and DNA repair proteins within the target cell [Lazebnik et al., Nature 371:346-7 (1994); Casciola-Rosen et al., J. Biol. Chem. 269:30757-60 (1994)]. For example, a RIP-like kinase, termed CARDIAk/RICK or RIP2 [see Thome et al., Current Biol. 8:885-88 (1998); McCarthy et al., J. Biol. Chem. 273:16968-75 (1998); Inohara et al., J. Biol. Chem. 273:12296-300 (1998)] has been shown to associate with caspase-1. These caspases are related to the *C. elegans* cell death gene product. Caspases are cysteine proteases that display aspartate specificity, and have been shown by a number of researchers to be crucial to apoptotic pathways. For a review, see Cryns et al., Genes & Development 12:1551-70 (1998). The natural substrates of the caspases are key regulatory and structural proteins, including protein kinases and proteins involved in DNA repair and cytoskeletal integrity.

There are a number of inhibitors of apoptosis (IAPs) that have been identified. Originally identified in baculoviruses, IAPs suppress the host cell death response, thereby allowing survival and propagation of the virus. To date, there are five human IAPs identified, which when expressed in human cells can inhibit apoptosis induced by a variety of stimuli. In addition, the IAPs have been shown to be fairly selective, with different pathways and/or enzymes being inhibited. Human XIAP, cIAP1 and cIAP2 are direct inhibitors of at least two caspase family members, caspase-3 and caspase-7.

Accordingly, the proteins involved in apoptosis and its regulation are of paramount interest, and it is an object of the invention to provide novel apoptosis proteins, herein termed Apop proteins, and in particular Apop1, Apop2, and Apop3 proteins and related molecules. It is a further object of the invention to provide recombinant nucleic acids encoding Apop proteins, and expression vectors and host cells containing the nucleic acid encoding them. A further object of the invention is to provide methods for screening for antagonists and agonists of Apop proteins.

SUMMARY OF THE INVENTION

According to the objects outlined above, the present invention provides recombinant nucleic acids encoding Apop proteins, and in particular Apop1, Apop2 and Apop3 proteins, that are at least about 85% identical to the amino acid sequence depicted in FIG. 2, FIG. 4, and FIG. 6 (SEQ ID NOS:2, 4 & 6), respectively. Similarly provided are recombinant nucleic acids at least about 85% identical to the nucleic acid sequence depicted in FIGS. 1, 3, and 5 (SEQ ID NOS:1, 3 & 5) or their complements. Expression vectors and host cells comprising the nucleic acids are also included.

In a further aspect, the invention provides methods of making Apop proteins, comprising providing a cell comprising an Apop protein encoding nucleic acid and subjecting the cell to conditions which allow the expression of Apop proteins.

In an additional aspect, the invention provides recombinant Apop proteins, that are at least about 85% identical to the amino acid sequences depicted in FIGS. 2, 4 and 6 (SEQ ID NOS:2, 4 & 6), respectively, and antibodies that will bind to the Apop1 proteins, Apop2 proteins and Apop3 proteins.

In a further aspect, the invention provides monoclonal and polyclonal antibodies binding to the apoptosis proteins Apop1, Apop2, and Apop3.

In a further aspect, the present invention provides methods for screening for a bioactive agent capable of binding to an Apop protein. The method comprises combining a candidate bioactive agent and an Apop protein and determining the binding of the candidate agent to the Apop protein.

In an additional aspect, the present invention provides methods for screening for agents capable of interfering with the binding of Apop3 and RIP. The methods comprise combining an Apop3 protein, a candidate bioactive agent and a RIP protein, and determining the binding of the Apop3 protein and the RIP protein.

In an additional aspect, the present invention provides methods for screening for agents capable of interfering with the binding of Apop1 and XIAP or Apop2 and XIAP. The methods comprise combining an Apop1 protein or Apop2 protein, a candidate bioactive agent and an XIAP protein, and determining the binding of the Apop1 protein and the XIAP protein or Apop2 protein and the XIAP protein.

In an additional aspect, the invention provides methods for screening for an bioactive agent capable of modulating the activity of an Apop protein. The method comprises the steps of adding a candidate bioactive agent to a cell comprising a recombinant nucleic acid encoding an Apop protein and determining the effect of the candidate bioactive agent on apoptosis.

In on aspect, a method for screening for a bioactive agent comprises providing a cell that expresses an expression profile gene selected from the group consisting of the expression profile genes set forth in FIGS. 1, 3, and 5 (SEQ ID NOS:1, 3 & 5).

In another aspect, a method for screening for a bioactive agent, comprises providing a cell that expresses an expression profile protein selected from the group consisting of the expression profile proteins having the amino acid sequence set forth in FIGS. 2, 4 and 6 (SEQ ID NOS:2, 4 & 6).

In another aspect, the invention provides a biochip comprising recombinant nucleic acids encoding Apop proteins. The recombinant nucleic acids, encoding Apop proteins and bound to the biochip, may be at least about 85% identical to the nucleic acid sequence depicted in FIGS. 1, 3 and 5 (SEQ ID NOS:1, 3 & 5) or their complements.

Other aspects of the invention will become apparent to the skilled artisan by the following description of the invention.

BRIEF DESCRIPTION OF THE DRAWINGS

FIG. 1 (SEQ ID NO:1) depicts the nucleotide sequence of human Apop1. The putative translation start codon (ATG) and translation termination codon (TGA) are underlined.

FIG. 2 (SEQ ID NO:2) depicts the amino acid sequence of human Apop1.

FIG. 3 (SEQ ID NO:3) depicts the nucleotide sequence of human Apop2. The putative translation start codon (ATG) and the translation termination codon (TGA) are underlined.

FIG. 4 (SEQ ID NO:4) depicts the amino acid sequence of human Apop2.

FIG. 5 (SEQ ID NO:5) depicts the nucleotide sequence of human Apop3.

FIG. 6 (SEQ ID NO:6) depicts the amino acid sequence of human Apop3.

FIG. 9 depicts the activation of apoptosis by Apop3 in Phoenix-A cells. Empty vector (Vector), Apop3, or Apop3 (1-436) (3 µg) was co-transfected with pGDB (1 µg) into Phoenix-A cells. Hoechst stained apoptotic Phoenix-A cells were examined and counted by fluorescence microscopy. The data are expressed as percentage of apoptotic cells among the total number of cells counted.

FIG. 10 depicts the activation of NFKκB by Apop3 in Phoenix-A cells. NFκB reporter activity was performed by transiently co-transfecting Phoenix-A cells with the indicated Apop3 expression vectors (3 µg) NFκB-dependent luciferase reporter plasmid (1 µg), and Renilla Luciferase expression vector (0.13 µg). Calcium phosphate precipitation method was used for transfection. The level of expressed tagged proteins was also monitored by Western blot analysis.

DETAILED DESCRIPTION OF THE INVENTION

Figures 7, 8:
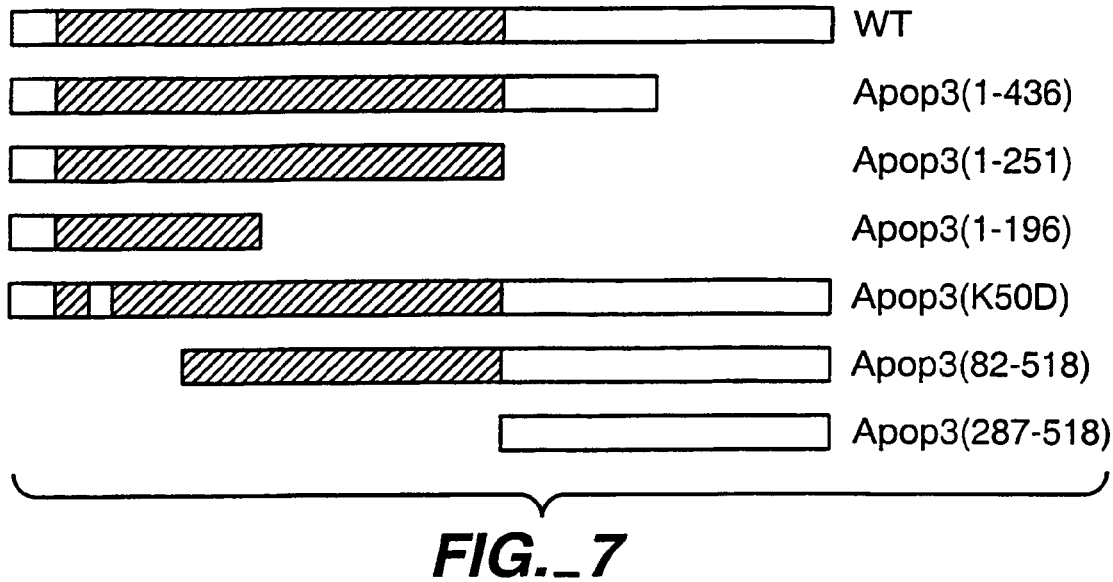
FIG. 7 depicts a schematic representation of Apop3 truncation mutants. The shaded area depicts the kinase homology domain. Apop3(K50D) has a K to D mutation at amino acid 5. WT, wild-type Apop3, i.e., the full-length protein.
FIG. 8 depicts a summary of binding results of Apop3 to RIP in the yeast two hybrid system. ++++, very strong interaction; +++, strong interaction, +, detectable interaction; –, no detectable interaction.

The present invention provides novel apoptosis proteins and nucleic acids which were initially identified using a yeast two-hybrid screening method. Traditionally, protein-protein interactions were evaluated using biochemical techniques, including chemical cross-linking, co-immunoprecipitation and co-fractionation and -purification. Recently genetic systems, including the "yeast two-hybrid system" have been described to detect protein-protein interactions. The basic system requires a protein-protein interaction between a "bait protein" and a "test protein" in order to turn on transcription of a reporter gene. See Fields et al., Nature 340:245 (1989); Vasavada et al., Proc. Natl. Acad. Sci. U.S.A. 88:10686 (1991); Fearon et al., Proc. Natl. Acad. Sci. U.S.A. 89:7958 (1992); Dang et al., Mol. Cell. Biol. 11:954 (1991); Chien et al., Proc. Natl. Acad. Sci. U.S.A., 88:9578 (1991); U.S. Pat. Nos. 5,283,173, 5,667,973, 5,468,614, 5,525,490, and 5,637,463; and U.S. patent application Ser. No. 09/050,863. In particular Apop1 and Apop2 were identified using XIAP as the "bait protein". Apop3 was identified using RIP as the "bait protein".

Thus, the present invention provides novel apoptosis proteins, termed Apop proteins and nucleic acids encoding them. Unless otherwise explicitly stated herein, the terms "Apop", "Apop protein" or grammatical equivalents thereof include Apop1 proteins, Apop2 proteins, and Apop3 proteins, the wild-type amino acid sequences of which are depicted in FIG. 2, FIG. 4, and FIG. 6 (SEQ ID NOS:2, 4 & 6) respectively. Similarly, the terms "Apop nucleic acid", "Apop DNA", "Apop nucleotide sequence" or grammatical equivalents thereof include nucleic acids which encode Apop1 proteins, Apop2 proteins and Apop3 proteins, the wild-type nucleic acid sequences of which are depicted in FIG. 1, FIG. 3, and FIG. 5 (SEQ ID NOS:1, 3 & 5), respectively.

In a preferred embodiment, the Apop proteins are from vertebrates and more preferably from mammals, including rodents (rats, mice, hamsters, guinea pigs, etc.), primates, farm animals (including sheep, goats, pigs, cows, horses, etc) and in the most preferred embodiment, from humans. However, using the techniques outlined below, Apop proteins from other organisms may also be obtained.

An Apop protein of the present invention may be identified in several ways. "Protein" in this sense includes proteins, polypeptides, and peptides. An Apop nucleic acid or Apop protein is initially identified by substantial nucleic acid and/or amino acid sequence homology to the sequences shown in FIGS. 1, 2, 3, 4, 5, and 6 (SEQ ID NOS:1-6). Such homology can be based upon the overal nucleic acid or amino acid sequence.

As used herein, a protein is an "Apop protein" if the overall homology of the protein sequence to the amino acid sequences shown in FIGS. 2, 4 and 6 (SEQ ID NOS:2, 4 & 6) is preferably greater than about 75%, more preferably greater than about 80%, even more preferably greater than about 85% and most preferably greater than 90%. In some embodiments the homology will be as high as about 93 to 95 or 98%.

Homology in this context means sequence similarity or identity, with identity being preferred. This homology will be determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc Natl. Acad. Sci. U.S.A. 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), or the Best Fit sequence program described by Devereux et al., Nucl. Acid Res. 12:387-95 (1984), preferably using the default settings, or by inspection.

In a preferred embodiment, similarity is calculated by FastDB based upon the following parameters: mismatch penalty of 1.0; gap size penalty of 0.33, joining penalty of 30.0 ("Current methods in Comparison and Analysis", Macromolecule Sequencing and Synthesis, selected methods and Applications, pp. 127-149 (1998), Alan R. Liss, Inc.). Another example of a useful algorithm is PILEUP, PILEUP creates a multiple sequence alignment from a group of related sequences using progressive, pariwise alignments. It can also plot a tree showing the clustering relationships used to create the alignment. PILEUP uses a simplification of the progressive alignment method of Feng and Doolittle, J. Mol. Envol. 35:351-60 (1987); the method is similar to that described by Higgins and Sharp CABIOS 5:151-3 (1989). Useful PILEUP parameters including a default gap weight of 3.00, a default gap length weight of 0.10, and weighted end gaps.

An additional example of a useful algorithm is the BLAST algorithm, described in Altschul et al., J. Mol. Biol. 215: 403-410 (1990) and Karlin et al., Proc. Natl. Acad. Sci. U.S.A. 90:5873-97 (1993). A particularly useful BLAST program is the WU-BLAST-2 program which was obtained from Altschul et al., Methods in Enzymology 266:460-480 (1996); http://blast.wustl/edu/blast/README. html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues dividing by the total number of residues of the "longer" sequence in the aligned region. The "longer" sequence is the one having the most actual residues in the aligned region (gaps introduced by WU-Blast-2 to maximize the alignment score are ignored).

In a similar manner, "percent(%) nucleic acid sequence identity" with respect to the coding sequence of the polypeptides identified herein is defined as the percentage of nucleotide residues in a candidate sequence that are identical with the nucleotide residues in the coding sequence of the Apop proteins (see FIGS. 1, 3, and 5 (SEQ ID NOS:1, 3 & 5)). A preferred method utilizes the BLASTN module of WU-BLAST-2 set to the default parameters, with overlap span and overlap fraction set to 1 and 0.125, respectively.

An additional useful algorithm is gapped BLAST as reported by Altschul et al., Nucl. Acid Res. 25:3389-3402 (1997). Gapped BLAST uses BLOSUM-62 substitution scores; threshold T parameter set to 9; the two-hit method to trigger ungapped extensions; charges gap lengths of κ a cost of 10+κ; $X_u$ set to 16, and $X_g$ set to 40 for database search stage and to 67 for the output stage of the algorithms. Gapped alignments are triggered by a score corresponding to ~22 bits.

The alignment may include the introduction of gaps in the sequences to be aligned. In addition, for sequences which contain either more or fewer amino acids than the protein sequences shown in FIGS. 2, 4 and 6 (SEQ ID NOS:2, 4 & 6) it is understood that the percentage of homology will be determined based on the number of homologous amino acids in relation to the total number of amino acids. Thus, for example, homology of sequences shorter than that shown in FIGS. 2, 4 and 6, as discussed below, will be determined using the number of amino acids in the shorter sequence.

In a preferred embodiment, the Apop protein binds to an IAP protein. Inhibitor-of-apoptosis (IAP) proteins are a novel family of anti-apoptotic proteins that were first identified in baculoviruses. Members of the human IAP family include, e.g., NAIP, HIAP-1 (human inhibitor of apoptosis protein-1), HIAP-2 (human inhibitor of apoptosis protein-2), c-IAP-1, c-IAP-2, and XIAP. They are thought to inhibit cell death via direct inhibition of caspases. Indeed, some IAP family proteins, e.g., c-IAP-1, c-IAP-2 and XIAP can bind to and inhibit the distal cell death proteases, caspases-3 and -7 (Roy et al., EMBO J., 16:6914-25 (1997); Takahashi et al., J. Biol. Chem. 273:7787-90 (1998)). Although IAPs are highly conserved through evolution, the mechanisms by which they interfere with the apoptotic cell death are not clear. There may be a number of unknown protein substrates for IAPs and agonistic or antagonistic proteins modulating the activity of IAPs.

In order to identify novel proteins interacting with IAPs, in particular with XIAP, we employed the yeast two-hybrid screening system. Using XIAP as the "bait protein" we identified two novel proteins interacting with XIAP, named Apop1 and Apop2.

In a preferred embodiment, the Apop protein is an Apop1 protein. The nucleotide sequence of Apop1 is depicted in FIG. 1 (SEQ ID NO:1) and the encoded protein in FIG. 2 (SEQ ID NO:2). A significant portion of the Apop1 nucleic acid and the encoded Apop1 protein has identity to human cathepsin B precursor protein and the corresponding DNA [Ritonja et al., FEBS Lett. 181:169-172 (1985); Chan et al., Proc. Natl. Acad. Sci. U.S.A. 83:7721-7725 (1986); Fong et al., Proc Natl. Acad. Sci. U.S.A. 83:2909-2913 (1986); Moin et al., Biochem. J. 285:427-434 (1992); Cao et al., Gene 139:163-169 (1994)]. Cathepsin B is a lysosomal thiol proteinase that may have additional extralysosomal functions. In particular, nucleotides 364 to 716 of the Apop1 nucleotide sequence depicted in FIG. 1 have >99% (352/353 nucleotide residues) identity to human cathepsin B (CTSB) mRNA (GenBank accession numbers NM_001908 and M14221). Likewise, on the amino acid level, the Apop1 amino acid sequence depicted in FIG. 2, shows 100% (109/109 amino acid residues) identity to human cathepsin B precursor protein (GenBank accession number P07858) and >99% (108/109 amino acid residues) identity to human cathepsin B precursor protein (GenBank accession number NP_001899). However, the remainder of the Apop1 protein and nucleic acid do not exhibit any homology to the known sequences. Thus the Apop1 nucleic acid sequence of the present invention may represent an alternatively spliced cathepsin B mRNA transcript and the encoded protein may have other biological activities when compared to cathepsin B.

On the nucleic acid level, there are a number of reported sequences including EST99543 and EST41374 that have homology to Apop1.

In a preferred embodiment, the Apop protein is an Apop2 protein. The nucleotide sequence of Apop2 is depicted in FIG. 3 (SEQ ID NO:3) and the encoded protein in FIG. 4 (SEQ ID NO:4). Apop2 nucleic acid and the encoded Apop2 protein have identity to human cathepsin F precursor protein and the corresponding NDA [Wang et al., J. Biol. Chem. 273:32000-8 (1998); Nagler et al., Biochem. Biophys. Res. Commun. 257:313-8 (1999); Santamaria et al., J. Chem. 274:13800-9 (1999); Wex et al., Biochem. Biophys. Res. Commun. 259:401-7 (1999); GenBank accession numbers AF071748, NM_003793, AF088886, AJ007331, and AF132894]. Cathepsin F is a novel papain-like cysteine proteinase, synthesized as a precursor protein, including a hydrophobic signal sequence, a pro-domain, and a catalytic region [Santamaria et al., J. Biol. Chem. 274:13800-9 (1999)]. Surprisingly, Apop2 has strong homology to several other cathepsins. Protein sequence comparison revealed 58% homology with cathepsin W; about 42-43% with cathepsin L, K, S, H, and O; and 38% with cathepsin B [Wang et al., J. Biol. Chem. 273:32000-8 (1998)]. The identification of Apop2 (cathepsin F) by binding to XIAP, represents the first time that a protein containing cathepsin homology has been shown to play a role in apoptosis.

On the nucleic acid level, there are a number of reported EST sequences that comprise portions of the Apop2 nucleic acid. These include EST43911/AA38898, yp01g08.r1/H39591, and EST91038/AA378321. In addition, there are several areas of homology to known cDNAs, including: 88% identity to a mouse mammary gland cDNA; (AA475592), 95% identity to a human cDNA clone (H15748), and a 88% identity to a mouse mammary gland cDNA (AA958896).

In a preferred embodiment, the Apop protein is an Apop3 protein. Using RIP as the "bait protein" in a yeast two-hybrid screening, Apop3 was identified. The nucleotide sequence of Apop3 is depicted in FIG. 5 (SEQ ID NO:5) and the encoded protein in FIG. 6 (SEQ ID NO:6). The human Apop3 appears to be expressed in heart, liver, pancreas, placenta and lung, but either weakly or not at all in brain. Apop3 has also been termed "RIP3" [see Yu et al., Current Biology 9:539-42 (1999); Sun et al., J. Biol. Chem. 274:16871-5 (1999)]. The N-terminal portion of Apop3, in particular amino acid residues 1-274, has homology to the kinase domain of RIP (34% identity and 60% similarity) and RIP2 (31% identity and 58% similarity) [see Sun et al., J. Biol. Chem. 274:16871-5 (1999)]. However, the C-terminal portion of Apop3 has no significant homology to any known proteins. Accordingly, Apop3 proteins may be identified in one aspect by significant homology to areas other than the kinase domain. This homology is preferably greater than about 60%, with greater than about 70 or 75% being particularly preferred and greater than about 80% being especially preferred. In some cases the homology will be greater than about 90 to 95 or 98%.

In addition, an Apop3 protein preferably also has significant homology to the kinase domain as described herein. This homology is preferably greater than about 75%, with greater than about 80% being particularly preferred and greater than about 85% being especially preferred. In some cases the homology will be greater than about 90 to 95 or 98%.

Apop proteins of the present invention may be shorter or longer than the amino acid sequences shown in FIGS. 2, 4, and 6 (SEQ ID NOS:2, 4 & 6). Thus, in a preferred embodiment, included within the definition of Apop proteins are portions or fragments of the sequences depicted herein. Portions or fragments of Apop proteins are considered Apop proteins if a) they share at least one antigenic epitope; or b) have at least the indicated homology; or c) preferably have Apop biological activity, e.g., including, but not limited to kinase activity, cell death activity, binding to XIAP or RIP, etc.

Well-known methods, such as in vitro manipulations of nucleic acids or PCR (polymerase chain reaction) are known in the art and are routinely used to generate portions or fragments of a desired nucleic acid sequence which then encodes a portion or a fragment of the desired protein. Generally, such portions of an Apop protein comprise at least 10%, preferably at least 20%, more preferably at least 25%, even more preferably at least 30% and most preferably at least 50% of the Apop protein.

In some embodiments, a portion of fragment of an Apop protein will comprise as much as 60 to 90 or 95% of the respective Apop protein.

In one embodiment, the portion or fragment of the respective Apop protein is contiguous to the Apop protein from which it is obtained. In another embodiment, the portion or fragment of the respective Apop protein is not contiguous to the Apop protein from which it is derived. In this embodiment, two or more parts of the Apop protein, for example, a fragment obtained from the N-terminus and a fragment obtained from the C-terminus are linked, whereby internal sequences are deleted.

In a preferred embodiment, the Apop proteins are derivative or variant Apop proteins. That is, as outlined more fully below, the derivative Apop peptide will contain at least one amino acid substitution, deletion or insertion, with amino acid substitutions being particularly preferred. The amino acid substitution, insertion or deletion may occur at any residue within the Apop peptide.

In addition, as is more fully outlined below, Apop proteins can be made that are longer than those depicted in FIGS. 2, 4, and 6 (SEQ ID NOS:2, 4 & 6), for example, by the addition of epitope or purification tags, the addition of other fusion sequences, etc.

Apop proteins may also be identified as being encoded by Apop nucleic acids. Thus, Apop proteins are encoded by nucleic acids that will hybridize to the sequence depicted in FIGS. 1, 3, and 5 (SEQ ID NOS:1, 3 & 5) or it s complement, as outlined herein.

In one preferred embodiment, the Apop proteins of the present invention may be used to generate polyclonal and monoclonal antibodies to Apop proteins, which are useful as described herein. The terms "Apop antibodies", "antibodies binding to Apop" or grammatical equivalents thereof include antibodies binding to Apop1 proteins, Apop2 proteins, and Apop3 proteins.

Apop antibodies usually are generated with an Apop protein having the amino acid sequence depicted in FIGS. 2, 4 and 6 (SEQ ID NOS:2, 4 & 6). In a preferred embodiment, Apop proteins corresponding to a portion of fragment of an Apop protein of which the amino acid sequence is depicted in FIGS. 2, 4, and 6, are used to generate antibodies. Methods for the preparation and purification of monoclonal and polyclonal antibodies are known in the art and e.g., are described in Harlow and Lane, *Antibodies: A Laboratory Manual* (New York:Cold Spring Harbor Laboratory Press, 1988). When the Apop protein is used to generate antibodies, the Apop protein must share at least one epitope or determinant with the full length protein shown in FIGS. 2, 4, and 6. By "epitope" or "determinant" herein is meant a portion of a protein which will generate and/or bind an antibody. Thus, in most instances, antibodies made to a smaller Apop3 protein will be able to bind to the full length protein.

In a preferred embodiment, the epitope is unique; that is, antibodies generated to a unique epitope show little or no cross-reactivity to other proteins. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies. The term "antibody" further comprises polyclonal antibodies and monoclonal antibodies, which can be agonist or antagonist antibodies.

The Apop antibodies of the invention specifically bind to Apop proteins. By "specifically bind" herein is meant that the antibodies bind to the protein with a binding constant in the range of at least $10^{-4}$ -$10^{-6}$ M$^{-1}$, with a preferred range being $10^{-7}$ 1$10^{-9}$ M$^{-1}$.

In a preferred embodiment, an Apop protein of the present invention may be identified by its immunological activity..

i.e., its ability to bind to an antibody specific for an epitope found within a protein comprising the amino acid sequence depicted in FIGS. 2, 4, and 6 (SEQ ID NOS:2, 4, & 6). The term "immunological activity" means the ability of the protein to cross react with an antibody which is specific for the protein comprising the amino acid sequence depicted in FIGS. 2, 4, and 6, i.e., an Apop protein antibody. Accordingly, a protein is an Apop protein, if the protein displays the immunlogical activity of a protein comprising the amino acid sequence depicted in FIGS. 2, 4, and 6.

In a preferred embodiment, Apop antibodies are provided. The antibodies may be polyclonal or monoclonal. In a preferred embodiment, the antibodies to Apop are capable of reducing or eliminating the biological function of Apop, as is described below. That is, the addition of anti-Apop antibodies (either polyclonal or preferably monoclonal) to Apop (or cells containing Apop) may reduce or eliminate the Apop activity. Generally, at least a 25% decrease in activity is preferred, with at least about 50% being particularly preferred and about a 95-100% decrease being especially preferred.

Monoclonal antibodies are directed against a single antigenic site or a single determinant on an antigen. Thus monoclonal antibodies, in contrast to polyclonal antibodies, which are directed against multiple different epitopes, are very specific. Monoclonal antibodies are usually obtained from the supernatant of hybridoma culture (see Kohler and Milstein, Nature 256:495-7 (1975); Harlow and Lane, *Antibodies: A Laboratory Manual* (New York: Cold Spring Harbor Laboratory Press, 1988).

In a preferred embodiment, the antibodies to Apop proteins are humanized. Using current monoclonal antibody technology one can produce a humanized antibody to virtually any target antigen that can be identified [Stein, Trends Biotechnol. 15:88-90 (1997)]. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) or the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature 321:522-525 (1986); Riechmann et al., Nature 332:323-329 (1988); and Presta, Curr. Op. Struct. Biol. 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., supra; Riechmann et al., supra; and Verhoeyen et al., Science, 239:1534-1536 (1988)], by substituting rodent CDRs or CDR sequences for the corresponding sequences of a human antibody. Additional examples of humanized murine monoclonal antibodies are also known in the art, e.g., antibodies binding human protein C [O'Connor et al., Protein Eng. 11:321-8 (1998)], interleukin 2 receptor [Queen et al., Proc. Natl. Acad. Sci., U.S.A. 86:10029-33 (1989)], and human epidermal growth factor receptor 2 [Carter et al., Proc. Natl. Acad. Sci. U.S.A. 89:4285-9 (1992)]. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogues sites in rodent antibodies.

Human antibodies can also be produced using various techniques known in the art, including phage display libraries [Hoogenboom and Winter, J. Mol. Biol. 227:381 (1991); Marks et al., J. Mol. Biol. 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., J. Immunol. 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10:779-783 (1992); Lonberg et al. Nature 368:856-859 (1994); Morrison, Nature 368:812-13 (1994); Fishwild et al., Nature Biotechnology 14:845-51 (1996); Neuberger, Nature Biotechnology 14:826 (1996); Lonberg and Huszar, Intern. Rev. Immunol. 13:65-93 (1995).

In a preferred embodiment, Apop nucleic acids are provided. An Apop nucleic acid of the present invention may be identified by its sequence identity to the nucleotide sequence depicted in FIGS. 1, 3, or 5 (SEQ ID NOS:1, 3 or 5) and may be referred to as having some "percent(%) sequence identity to allor a portion of the nucleotide sequence depicted in FIGS. 1, 3, or 5. Sequence identity, when referring to nucleic acid, means that the sequences being compared have nucleotides at corresponding positions which are identical. The sequence identity of an Apop nucleic acid is commensurate with the sequence identity of Apop proteins but takes into account the degeneracy in the genetic code and codon bias of different organisms. Accordingly, the sequence identity for Apop nucleic acids may differ from the sequence identity for Apop proteins. Thus, the nucleic acid sequence homology may be either lower or higher than that of the protein sequence. Thus the homology of the nucleic acid sequence as compared to the nucleic acid sequences of FIGS. 1, 3, and 5 is preferably greater than 75%, more preferably greater than about 80%, particularly greater than about 85% and most preferably greater than 90%. In some embodiments the homology will be as high as about 93 to 95 or 98%.

In a preferred embodiment, an Apop nucleic acid encodes an Apop protein. As will be appreciated by those in the art, due to the degeneracy of the genetic code, an extremely large number of nucleic acids may be made, all of which encode the Apop proteins of the present invention. Thus, having identified a particular amino acid sequence, those skilled in the art could make any number of different nucleic acids, by simply modifying the sequence of one or more codons in a way which does not change the amino acid sequence of the Apop.

In one embodiment, the nucleic acid homology is determined through hybridization studies. Thus, for example, nucleic acids which hybridize under high stringency to the nucleic acid sequences shown in FIGS. 1, 3, and 5 (SEQ ID NOS:1, 3 or 5) or their complements are considered an Apop gene. High stringency conditions are known in the art; see for example Sambrook et al., *Molecular Cloning: A Laboratory Manual* (New York: Cold Spring Harbo Laboratory Press, 1989) and Ausubel et al., *Short Protocols in Molecular Biology* (John Wiley & Sons, Inc., 1995), both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology:Hybridization with Nucleic Acid Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Sambrook et al., supra, Ausubel et al., supra, and Tijssen, supra.

The Apop proteins and nucleic acids of the present invention are preferably recombinant. As used herein, and defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequences depicted in FIGS. 1, 3, and 5 also include the complement of these sequences. By the term "recombinant nucleic acid" herein is meant nucleic acid, originally formed in vitro, in general, by the manipulation of nucleic acid by endonucleases, in a form not normally found in nature. Thus an isolated Apop nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an Apop protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

Also included within the definition of Apop proteins of the present invention are amino acid sequence variants. These variants fall into one or more of three classes: substitutional, insertional or deletional variants. These variants ordinarily are prepared by site specific mutagenesis of nucleotides in the DNA encoding the Apop protein, using cassette or PCR mutagenesis or other techniques will known in the art, to produce DNA encoding the variant, and thereafter expressing the recombinant DNA in cell culture as outlined above. However, variant Apop protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the Apop protein amino acid sequence. The variants typically exhibit the same qualitative biological activity as the naturally occurring analogue. although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed Apop variants screened for the optimal combination of desired activity. Techniques for making substitution mutations at predetermined sites in DNA having a known sequence are well known, for example, M13 primer mutagenesis and PCR mutagenesis. Screening of the mutants is done using assays of Apop protein activities.

Amino acid substitutions are typically of single residues; insertions usually will be on the order of from about 1 to 20 amino acids, although considerably larger insertion may be tolerated. Deletions range from about 1 to 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the Apop protein are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the Apop proteins as needed. Alternatively, the variant may be designed such that the biological activity of the Apop protein is altered. For example, glycosylation sites may be altered or removed. Similarly, e.g., mutations within the cysteine protease domain of Apop1 or Apop2 or within the kinase domain of Apop3 may be made.

Covalent modifications of Apop polypeptides are included within the scope of this invention. One type of covalent modification includes reacting targeted amino acid residues of an Apop polypeptide with an organic derivatizing agent that is capable of reacting with selected side chains or the N-or C-terminal residues of an Apop polypeptide. Derivatization with bifunctional agents is useful, for instance, for crosslinking Apop to a water-soluble support matrix or surface for use in the method for purifying anti-Apop antibodies or screening assays, as is more fully described below. Commonly used crosslinking agents include, e.g., 1,1-bis(diazoacetyl)-2-phenylethane, glutaraldehyde, N-hydroxy-succinimide esters, for example, esters with 4-azidosalicyclic acid, homobifunctional imidoesters, including disuccinimidyl esters such as 3,3'-dithiobis(succinimidylpropionate), bifuncational maleimides such as bis-N-maleimido-1,8-octane and agents such as methyl-3-[(p-azidophenyl)dithio]propioimi-data.

Other modifications include deamidation of gluatminyl and asparaginyl residues to the corresponding glutamyl and aspartyl residues, respectively, hydroxylation of proline and lysine, phosphorylation of hydroxyl groups of seryl or threonyl residues, methylation of the amino groups of lysine, arginine, and histidine side chains [T. E. Creighton, *Proteins: Structure and Molecular Properties*, W. H. Freeman & Co., San Francisco, pp. 79-86 (1983)], acetylation of the N-terminal amine, and amidation of any C-terminal carboxyl group.

Another type of covalent modification of the Apop polypeptide included within the scope of this invention comprises altering the native glycosylation pattern of the polypeptide. "Altering the native glycosylation pattern" is intended for purposes herein to mean deleting one or more carbohydrate moieties found in native sequence Apop polypeptide, and/or adding one or more glycosylation sites that are not present in the native sequence Apop polypeptide.

Addition of glycosylation sites to Apop polypeptides may be accomplished by altering the amino acid sequence thereof. The alteration may be made, for example, by the addition of, or substitution by, one or more serine or threonine residues to the native sequence Apop polypeptide (for O-linked glycosylation sites). The Apop amino acid sequence may optionally be altered through changes at the DNA level, particularly by mutating the DNA encoding the Apop polypeptide at preselected bases such that codons are generated that will translate into the desired amino acids.

Another means of increasing the number of carbohydrate moieties on the Apop polypeptide is by chemical or enzymatic coupling of glycosides to the polypeptide. Such methods are described in the art, e.g., in WO 87/05330 published 11 Sep. 1987and in Aplin and Wriston, CRC Crit. Rev. Biochem., pp. 259-306 (1981).

Removal of carbohydrate moieties present on the Apop polypeptides may be accomplished chemically or enzymatically or by mutational substitution of codons encoding for amino acids residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Another type of covalent modification of Apop comprises linking the Apop polypeptide to one of a variety of nonproteinacecous polymers, e.g., polyethylene glycol, polypropylene glycol, or polyoxyalkylenes, in the manner set forth in U.S. Pat. Nos. 4,648,835; 4,496,689; 4,301,144; 4,670,417; 4,791,192 or 4,179,337.

Apop polypeptides of the present invention may also be modified in a way to form chimeric molecules comprising an Apop polypeptide fused to another, heterologous polypeptide or amino acid sequence.

In one embodiment, such a chimeric molecule comprises a fusion of an Apop polypeptide with a tag polypeptide which provides an epitope to which an anti-tag antibody can selectively bind. The epitope tag is generally placed at the amino-or carboxyl-terminus of the Apop polypeptide. The presence of such epitope-tagged forms of an Apop polypeptide can be detected using an antibody against the tag polypeptide. Also, provision of the epitope tag enables the Apop polypeptide to be readily purified by affinity purification using an anti-tag antibody or another type of affinity matrix that binds to the epitope tag. In an alternative embodiment, the chimeric molecule may comprise a fusion of an Apop polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptides and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 eptiope peptide [Martin et al., Science, 255:192-194 (1992)]; tublin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)].

Also included with the definition of Apop protein are other Apop proteins of the Apop family, and Apop proteins from other organisms, which are cloned and expressed as outlined below. Thus, probe or degenerate polymerase chain reaction (PRC) primer sequences may be used to find other related Apop proteins from humans or other organisms. As will be appreciated by those in the art, particularly useful probe and/or PCR primer sequences include the unique areas of the Apop nucleic acid sequence. As is generally known in the art, preferred PCR primers are from about 15 to about 35 nucleotides in length, with from 20 to about 30 being preferred, and may contain inosine as needed. The conditions for the PCR reaction are well known in the art.

In another preferred embodiment, new members within an Apop family are identified within the different cells or tissues of the same organism. The amino acid sequences of individual members are aligned and analyzed as described above. Amino acid sequences which are identical among those family members are used to design PCR primers. These PCR primers take the degeneracy of the genetic code into consideration and thus, may e.g., incorporate inosine at the third codon position. Similarly, PCR primers are designed based on the alignment and analysis of the respective nucleic acid sequences. Thus, PCR primers are designed to bind to conserved nucleotide sequences shared by different members of the Apop family. In this embodiment, nucleotide sequences for all members of the Apop family, i.e., known and unknown members, sharing the respective nucleotide sequences to which the PCR primers bind, are generated by PCR. Subsequent subcloning and DNA analysis of the generated DNA fragments, as is well known in the art and e.g. described in Sambrook et al., *Molecular Cloning: A Laboratory Manual* (New York: Cold Spring Harbor Laboratory Press, 1989) and Ausubel et al., *Short Protocols in Molecular Biology* (John Wiley & Sons, Inc., 1995) identifies known and/or new members of the Apop family.

Once the Apop nucleic acid is identified, it can be cloned and, if necessary, its constituent parts recombined to form the entire Apop nucleic acid. Once isolated from its natural source, e.g., contained within a plasmid or other vector or excised therefrom as a linear nucleic acid segment, the recombinant Apop nucleic acid can be further-used as a probe to identify and isolate other Apop nucleic acids. It can also be used as a "precursor" nucleic acid to make modified or variant Apop nucleic acids and proteins.

Using the nucleic acids of the present invention which encode an Apop protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the Apop protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional regulatory nucleic acid will generally be appropriate to the host cell used to express the Apop protein, as will be appreciated by those in the art; for example, transcriptional and translational regulatory nucleic acid sequences from *Bacillus* are preferably used to express the Apop protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancers or activator sequences. In a preferred embodiment, the regulatory sequences include a promoter and transcriptional start and stop sequences.

Promoter sequences include constitutive and inducible sequences. The promoters may be either naturally occurring promoters, hybrid or synthetic promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors and appropriate selection and screening protocols are well known in the art and are described in e.g., Mansour et al., *Cell*, 51:503 (1988) and Murray, *Gene Transfer and Expression Protocols, Methods in Molecular Biology*, Vol. 7 (Clifton: Humana Press, 1991).

In addition, in a preferred embodiment, the expression vector contains a selection gene to allow the selection of transformed host cells containing the expression vector, and particularly in the case of mammalian cells, ensures the stability of the vector, since cells which do not contain the vector will generally die. Selection genes are well known in the art and will vary with the host cell used. By "selection gene" herein is meant any gene which encodes a gene product that confers resistance to a selection agent. Suitable selection agents include, but are not limited to, neomycin (or its analog G418), blasticidin S, histinidol D, bleomycin, puromycin, hygromycin B, and other drugs.

In a preferred embodiment, the expression vector contains a RNA splicing sequence upstream or downstream of the gene to be expressed in order to increase the level of gene expression. See Barret et al., Nucleic Acids Res. 1991; Groos et al., Mol. Cell. Biol. 1987; and Budiman et al., Mol. Cell. Biol. 1988.

A preferred expression vector system is a retroviral vector system such as is generally described in Mann et al., Cell, 33:153-9 (1993); Pear et al., Proc. Natl. Acad. Sci. U.S.A., 90(18):8392-6 (1993); Kitamura et al., Proc. Natl. Acad. Sci. U.S.A., 92:9146-50 (1995); Kinsella et al., Human Gene Therapy, 7:1045-13; Hoffmann et al., Proc. Natl. Acad. Sci. U.S.A., 93:5185-90; Choate et al., Human Gene Therapy, 7:2247 (1996); PCT/US97/01019 and PCT/US97/01048, and references cited therein, all of which are hereby expressly incorporated by reference.

The Apop proteins of the present invention are produced by culturing a host cell transformed with nucleic acid, preferably an expression vector, containing nucleic acid encoding an Apop protein, under the appropriate conditions to induce or cause expression of the Apop protein. The conditions appropriate for Apop protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral system used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melanogaster* cells, *Saccharomyces cerevisiae* and other yeasts, *E. coli*, *Bacillus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines, Jurkat cells, mast cells and other endocrine and exocrine cells, and neuronal cells. See the ATCC cell line catalog, hereby expressly incorporated by reference.

In a preferred embodiment, the Apop proteins are expressed in mammalian cells. Mammalian expression systems are also known in the art, and include retroviral systems. A mammalian promoter is any DNA sequence capable of binding mammalian RNA polymerase ad initiating the downstream (3') transcription of a coding sequence for Apop3 protein into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived from SV40.

The methods of introducing exogenous nucleic acid into mammalian hosts, as well as other hosts, is well known in the art, and will vary with the host cell used. Techniques include extran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, Apop proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of Apop3 protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galatose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the Apop protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcuim chloride treatment, electroporation, and others.

In one embodiment, Apop proteins are produced in insect cells. Expression vectors for the transformation of insect cells, and in particular, baculovirus-based expression vectors, are well known in the art and are described e.g., in O'Reilly et al., *Baculovirus Expression Vectors: A Laboratory Manual* (New York: Oxford University Press, 1994).

In a preferred embodiment, Apop protein is produced in yeast cells. Yeast expression systems are well known in the art, and include expression vectors for *Saccharomyces cerevisiae, Candida albicans* and *C. maltose, Hansenula polymorpha, Kluyveromyces fragilis* and *K. lactis, Pichia guilerimondii* and *P. pastoris, Schizosaccharomyces pombe*, and *Yarrowia lipolytica*. Preferred promoter sequences for expression in yeast include the inducible GAL1, 10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The Apop protein may also be made as a fusion protein, using techniques well known in the art. Thus, for example, for the creation of monoclonal antibodies, if the desired epitope is small, the Apop protein may be fused to a carrier protein to form an immunogen. Alternatively, the Apop protein may be made as a fusion protein to increase expression, or for other reasons. For example, when the Apop protein is an Apop peptide, the nucleic acid encoding the peptide may be linked to other nucleic acid for expression purposes.

In one embodiment, the Apop nucleic acids, proteins and antibodies of the invention are labeled. By "labeled" herein is meant that nucleic acids, proteins and antibodies of the invention have at least one element, isotope or chemical compound attached to enable the detection of nucleic acids, proteins and antibodies of the invention. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In the preferred embodiment, the Apop protein is purified or isolated after expression. Apop proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the Apop protein may be purified using a standard anti-Apop3 antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the Apop3 protein. In some instances no purification will be necessary.

Once expressed and purified if necessary, the Apop proteins and nucleic acids are useful in a number of applications.

In a preferred embodiment, the Apop proteins are used to make Apop antibodies. Apop antibodies find use in a number of applications. For example, the Apop antibodies may be coupled to standard affinity chromatography columns and used to purify Apop proteins. The antibodies may also be used as blocking polypeptides, as outlined above, since they will specifically bind to the Apop protein.

In a preferred embodiment, the Apop protein and/or Apop nucleic acid is used to generate antibodies, for example for immunotherapy. By "immunotherapy" is meant treatment of apoptosis with an antibody raised against Apop proteins. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with an Apop antigen to which antibodies are raised. As appreciated by one of ordinary skill in the art, the Apop antigen may be provided by injecting an Apop polypeptide against which antibodies are desired to be raised into a recipient, or contacting the recipient with an Apop nucleic acid, capable of expressing the Apop antigen, under conditions for expression of the Apop antigen.

In a preferred embodiment, a therapeutic compound is conjugated to an antibody, preferably an Apop antibody. The therapeutic compound may be a cytotoxic agent. In this method, targeting the cytotoxic agent to apoptotic cells or tumor tissue or cells, results in a reduction in the number of afflicted cells, thereby reducing symptoms associated with apoptosis and cancer. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against Apop proteins, or binding of a radionuclide to a chelating agent that has been covalently attached to the antibody.

In a preferred embodiment, Apop genes are administered as DNA vaccines, either single genes or combinations of Apop genes. Naked DNA vaccines are generally known in the art; see Brower, Nature Biotechnology 16:1304-1305 (1998). Methods for the use of genes as DNA vaccines are well known to one of ordinary skill in the art, and include placing an Apop gene or portion of an Apop gene under the control of a promoter for expression in a patient. The Apop gene used for DNA vaccines can encode full-length Apop proteins, but more preferably encodes portions of the Apop proteins including peptides derived from the Apop protein. In a preferred embodiment a patient is immunized with a DNA vaccine comprising a plurality of nucleotide sequences derived from a Apop gene. Similarly, it is possible to immunize a patient with a plurality of Apop genes or portions thereof, as defined herein. Without being bound by theory, following expression of the polypeptide encoded by the DNA vaccine, cytotoxic T-cells, helper T-cells and antibodies are induced which recognize and destroy or eliminate cells expressing Apop proteins.

In a preferred embodiment, the DNA vaccines include a gene encoding an adjuvant molecule with the DNA vaccine. Such adjuvant molecules include cytokines that increase the immunogenic response to the Apop polypeptide encoded by the DNA vaccine. Additional or alternative adjuvants are known to those of ordinary skill in the art and find use in the invention.

In a preferred embodiment, the Apop proteins, nucleic acids, modified proteins and cells containing the native or modified Apop proteins are used in screening assays. Identification of the Apop proteins permits the design of drug screening assays for compounds that modulate Apop activity.

Screens are designed to first find candidate agents that can bind to Apop proteins, and then these agents are used in assays that evaluate the ability of the candidate agent to modulate Apop activity. The terms "binding to Apop" and "modulating Apop activity" or grammatical equivalents thereof comprise binding to Apop1 proteins, Apop2 proteins, Apop3 proteins, and modulating Apop1 protein activity, Apop2 protein activity, and Apop3 protein activity. As will be appreciated by those in the art, there are a number of different assays which may be run; binding assays and activity assays.

In a preferred embodiment, the methods comprise combining an Apop protein and a candidate bioactive agent, and determining the binding of the candidate agent to the Apop protein. Preferred embodiments utilize the human Apop protein, although other mammalian Apop proteins may also be used, including rodents (mice, rats, hamsters, guinea pigs, etc.) farm animals (cows, sheep, pigs, horses, etc.) and primates. These latter embodiments may be preferred in the development of animal models of human disease. In some embodiments, as outlined herein, variant or derivative Apop proteins may be used, including deletion Apop proteins as outlined above. Furthermore, included within the definition of Apop proteins are portions or fragments of Apop proteins; that is, either the full-length protein may be used, or, as outlined above, portions of fragments thereof. In addition, the assays described herein may utilize either isolated Apop proteins or cells comprising the Apop proteins.

Generally, in a preferred embodiment of the methods herein, the Apop protein or the candidate agent, is nondiffusably bound to an insoluble support having isolated sample receiving areas (e.g. a microtiter plate, an array, etc.). The insoluble support may be made of any composition to which the Apop protein or the candidate agent can be bound, is readily separated from soluble material, and is otherwise compatible with the overall method of screening. The surface of such supports may be solid or porous and of any convenient shape. Examples of suitable insoluble supports include microtiter plates, arrays, membranes and beads. There are typically made of glass, plastic (e.g., polystyrene) polysaccharides, nylon or nitrocellulose, teflon198 , etc. Microtiter plates and arrays are especially convenient because a large number of assays can be carried out simultaneously, using small amounts of reagents and samples. The particular manner of binding the Apop protein or the candidate agent is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the Apop protein or candidate agent, excess unbound material is removed by washing. The sample receiving areas may then be blocked through incubation with bovine serum albumin (BSA), casein or other innocuous protein or other moiety.

In a preferred embodiment, the Apop protein is bound to the support, and a candidate bioactive agent is added to the assay. Alternatively, the candidate agent is bound to the support and the Apop protein is added. Novel binding agents include specific antibodies, non-natural binding agents identified in screens of chemical libraries, peptide analogs, etc. Of particular interest are screening assays for agents that have a low toxicity for human cells. Determination of the binding of an Apop protein and a candidate agent is done using a wide variety of assays, including, but not limited to labeled in vitro protein-protein binding assays, electrophoretic mobility shift assays, immunoassays for protein binding, functional assays (phosphoylation assays, etc.) and the like.

The term "candidate bioactive agent" or "exogeneous compound" as used herein includes any molecule, e.g., protein, oligopeptide, small organic molecule, polysaccharide, polynucleotide, lipid, etc., or mixtures thereof, with the capability of directly or indirectly altering the bioactivity of Apop. Generally a plurality of assay mixtures is run in parallel with different candidate agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety or organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bounds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acids" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening against Apop. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate radomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment a library of protein encoding nucleotide sequences is added to the host cell comprising the vector composition of the invention. The library of protein encoding nucleotide sequences may be obtained from genomic DNA, from cDNAs or from random nucleotides. Particularly preferred in this embodiment are libraries encoding bacterial, fungal, viral, and mammalian proteins and peptides, with the latter being preferred, and human encoding proteins and peptides being especially preferred. As described above and as known in the art the protein and peptide encoding nucleotide sequences may be inserted into any vector suitable for expression in mammalian cells.

In a preferred embodiment, the candidate bioactive agents are nucleic acids. By "nucleic acid" or "oligonucleotide" or grammatical equivalents herein means at least two nucleotides convalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49)10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), pohsphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference).

Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleoside 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in antisense Research", Ed. Y. S. Sanghui and P. Can Cook. Nucleic acids containing one or more carbocyclic sugars are also included within the definition of nucleic acids (see Jenkins et al., Chem. Soc. Rev. (1995) pp169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxathine, isocytosine, isoguanine, etc.

As described above generally for proteins, nucleic acid candidate bioactive agents may be naturally occurring nucleic acids, random nucleic acids, or "biased" random nucleic acids. For example, digests of prokaryotic or eukaryotic genomes may be used as is outlined above for proteins.

In a preferred embodiment, the candidate bioactive agents are obtained from combinatorial chemical libraries, a wide variety of which are available in the literature. By "combinatorial chemical library" herein is mean a collection of diverse chemical compounds generated in a defined or random manner, generally by chemical synthesis. Millions of chemical compounds can be synthesized through combinatorial mixing.

The determination of the binding of the candidate bioactive agent to the Apop protein may be done in a number of ways. In a preferred embodiment, the candidate bioactive agent is labeled, and binding determined directly. For example, this may be done by attaching all or a portion of the Apop protein to a solid support, adding a labeled candidate agent (for example a candidate agent comprising a fluorescent label), washing off excess reagent, and determining whether the label is present on the solid support. Various blocking and washing steps may be utilized as is known in the art.

By "labeled" herein is meant that the candidate bioactive agent is either directly or indirectly labeled with a label which provides a detectable signal, e.g. a radioisotope (such as $^3$H, $^{14}$C, $^{32}$P, $^{33}$P, $^{35}$S, or $^{125}$I), a fluorescent or chemiluminescent compound (such as fluorescein isothiocyanate, rhodamine, or luciferin), an enzyme (such as alkaline phosphatase, beta-galactosidase or horseradish peroxidase), antibodies, particles such as magnetic particles, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. the Apop protein), such as an antibody, peptide, binding partner, ligand, etc. In a preferred embodiment, the competitor for Apop3 is RIP (Stanger et al., supra). In another preferred embodiment, the competitor for Apop1 and Apop2 is XIAP (Deveraux et al., Nature 388:300-303 (1997). Under certain circumstances, there may be competitive bindings as between the bioactive agent and the binding moiety, with the binding moiety displacing the bioactive agent.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4° C. and 40° C. Incubation periods are selected for optimum activity, but may also optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the Apop protein and thus is capable of binding to, and potentially modulating, the activity of the Apop protein. In this embodiment, either component can be labeled. Thus, for example, if the competitor is labeled, the presence of label in the wash solution indicates displacement by the agent. Alternatively, if the candidate bioactive agent is labeled, the presence of the label onthe support indicates displacement.

In an alternative embodiment, the candidate bioactive agent is added first, with incubation and washing, followed by the competitor. The absence of binding by the competitor may indicate that the bioactive agent is bound to the Apop protein with a higher affinity. Thus, if the candidate bioactive agent is labeled, the presence of the label on the support, coupled with a lack of competitor binding, may indicate that the candidate agent is capable of binding to the Apop protein.

In a preferred embodiment, the methods comprise differential screening to identify bioactive agents that are capable of modulating the activity of the Apop proteins. In this embodiment, the methods comprise combining an Apop protein and a competitor in a first sample. A second sample comprises a candidate bioactive agent, an Apop protein and a competitor. Addition of the candidate bioactive agent is performed under conditions which allow the modulation of the Apop protein. The binding of the competitor is determined for both samples, and a change, or difference in binding between the two samples indicates the presence of an agent capable of binding to the Apop protein and potentially modulating its activity. That is, if the binding of the competitor is different in the second sample relative to the first sample, the agent is capable of binding to the Apop protein.

Another preferred embodiment utilizes differential screening to identify drug candidates that bind to the native Apop protein, but cannot bind to modified Apop proteins. The structure of the Apop protein may be modeled, and used in rational drug design to synthesize agents that interact with that site. Drug candidates that affect Apop bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of Apop may also be done. In a preferred embodiment, methods for screening for a bioactive agent capable of modulating the activity of Apop comprise the steps of adding a candidate bioactive agent to a sample of Apop, as above, and determining an alteration in the biological activity of Apop. "Modulating the activity of Apop" includes an increase in activity, a decrease in activity, or a change in the type or kind of activity present. Thus, in this embodiment, the candidate agent should both bind to Apop (although this may not be necessary), and alter its biological or biochemical activity as defined herein. The methods include both in vitro screening methods, as are generally outlined above, and in vivo screening of cells for alterations in the presence, distribution, activity or amount of Apop.

Thus, in this embodiment, the methods comprise combining an Apop sample and a candidate bioactive agent, and evaluating the effect on apoptosis. By "Apop activity" or grammatical equivalents herein is meant one or more of the biological activities of Apop1, Apop2, and Apop3. Apop1's and Apop2's biological activity, e.g., comprises the ability to affect apoptosis. Apop3's biological activities, include, but are not limited to, its kinase activity, its ability to activate NF-κB, its ability to activate caspase-3, and its ability to affect apoptosis. Apop3 kinase activity may be assayed using known serine/threonine kinase assays; see Thome et al., J. Exp. Med 181:1997 (1995); del Peso et al., Science 278:687 (1997), and others. Similarly, death domain assays are known in the art.

In a preferred embodiment, the activity of the Apop protein is increased; in another preferred embodiment, the activity of the Apop protein is decreased. Thus, bioactive agents that are antagonists are preferred in some embodiments, and bioactive agents that are agonists may be preferred in other embodiments.

In a preferred embodiment, the invention provides methods for screening for bioactive agents capable of modulating the activity of an Apop protein. The methods comprise adding a candidate bioactive agent, as defined above, to a cell comprising Apop proteins. Preferred cell types include almost any cell as defined above for host cells. Preferred cells include, but are not limited to prokaryotic cells and eukaryotic cells, with mammalian cells and particularly human cells being preferred.

The cells contain a recombinant nucleic acid that encodes an Apop protein. In a preferred embodiment, a library of candidate agents is tested on a plurality of cells. By a "plurality of cells" herein is meant roughly from about $10^3$ cells to $10^8$ or $10^9$, with from $10^6$ to $10^8$ being preferred.

In some embodiments, the assays include exposing the cells to an apoptosis agent that will induce apoptosis in control cells, i.e. cells of the same type but that do not contain the exogeneous nucleic acid encoding an Apop. Suitable apoptosis inducing agents are known in the art. Alternatively, the cells may be exposed to conditions that normally result in apoptosis, and changes in the normal apoptosis progression are determined. Alternatively, the cells into which the Apop nucleic acids are introduced, normally undergo apoptosis, and thus changes (for example, inhibition of apoptosis) are determined. Optionally, the cells normally do not undergo apoptosis, and the introduction of a candidate agent causes apoptosis.

Thus, the effect of the candidate agent on apoptosis is then evaluated.

Methods for the detection of apoptosis may be done as will be appreciated by those in the art. In one embodiment, indicators of apoptosis are used. Suitable apoptosis labels include, but are not limited to, DAPI. Accordingly, these agents can be used as an affinity ligand, and attached to a solid support such as a bead, a surface, etc. and used to pull out cells that are undergoing apoptosis. Similarly, these agents can be coupled to a fluorescent dye such as PerCP, and then used as the basis of a fluorescent-activated cell sorting (FACS) separation.

Sensitive assays that measure various biological and morphological hallmarks of the apoptotic process are known in the art. For example, a monoclonal antibody which can be used to detect cleavage of poly (ADP-ribose) polymerase, CCP32/Caspase-3 fluorescent and colorimetric assay kits, and a FLICE/caspase-8 fluorescent assay kit are commercially available (Clontech Laboratories, Inc.). Annexin V apoptosis assays, measuring the translocated phosphatidylserine (PS) are described, e.g., in Dachary-Prigent et al., Blood 81:2554-65 (1993); Thiagarajan and Tait, J. Biol. Chem. 265:17420-3 (1990); and Zhang et al., Biotechniques 23:525-31 (1997). Identification of apoptosis in situ via specific labeling of nuclear DNA fragmentation is described in Gavrieli et al., J. Cell Biol. 119:493-50 (1992).

In a preferred embodiment, bioactive agents identified by one of the methods outlined above, may be compounds showing pharmacological activity or therapeutical activity. Compounds with pharmacological activity are able to enhance or interfere with the activity of the Apop protein. The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of a therapeutically active compound in the formulation may vary from about 0.1-100 wt %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Without being bound by theory, it appears that the Apop proteins are important proteins in apoptosis. Accordingly, disorders based on mutant or variant Apop genes may be determined. In one embodiment, the invention provides methods for identifying cells containing variant Apop genes comprising determining all or part of the sequence of at least one endogenous Apop genes in a cell. As will be appreciated by those in the art, this may be done using any number of sequencing techniques. In a preferred embodiment, the invention provides methods of identifying the Apop genotype of an individual comprising determining all or part of the sequence of at least one Apop gene of the individual.

This is generally done in at least one tissue of the individual, and may include the evaluation of a number of tissues or different samples of the same tissue. The method may include comparing the sequence of the sequenced Apop gene to a known Apop gene, i.e. a wild-type gene (e.g., those nucleic acid sequences depicted in FIGS. 1, 3, and 5) and determining if any differences exist. This can be dones using any number of known homology programs, such as Bestfit, etc. In a preferred embodiment, the presence of a difference in the sequence between the Apop gene of the patient and the known Apop gene is indicative of a disease state or a propensity for a disease state, as outlined herein.

The present discovery relating to the role of Apop in apoptosis thus provides methods for inducing or preventing apoptosis in cells. In a preferred embodiment, the Apop proteins, and particularly Apop fragments, are useful in the study or treatment of conditions which are mediated by apoptosis, i.e. to diagnose, treat or prevent apoptosis-mediated disorders. Thus, "apoptosis mediated disorders" or "disease state" include conditions involving both insufficient apoptosis, including cancer, autoimmune disorders and sustained viral infections, and excessive apoptosis, including inappropriate cell loss and degenerataive disorders.

In one embodiment, methods of modulating apoptosis in cells or organisms are provided. In one embodiment, the methods comprise administering to a cell an anti-Apop antibody that reduces or eliminates the biological activity of the endogenous Apop protein. Alternatively, the methods comprise administering to a cell or organism a recombinant nucleic acid encoding an Apop protein. As will be appreciated by those in the art, this may be accomplished in any number of ways. In a preferred embodiment, the activity of Apop is increased by increasing the amount of Apop in the cell, for example by overexpressing the endogenous Apop or by administering a gene encoding Apop, using known gene-therapy techniques, for example. In a preferred embodiment, the gene therapy techniques include the incorporation of the exogeneous gene using enhanced homologous recombination (EHR), for example as described in PCT/US93/03868, hereby incorporated by reference in its entirety.

In one embodiment, the invention provides methods for diagnosing an Apop mediated disorder in an individual. The methods comprise measuring the activity and expression of Apop in a tissue from an individual or patient, which may include a measurement of the amount or specific activity of Apop. This activity is quantified and compared to the activity of Apop from either an unaffected second individual or from an unaffected tissue from the first individual. When these activities are different, the first individual may be at risk for an Apop mediated disorder. In this way, for example, monitoring of various disease conditions may be done, by monitoring the levels of Apop. Similarly, Apop levels may correlate to the diseases and conditions enumerated above.

In one aspect, the expression levels of Apop genes are determined in different patient samples or cells for which either diagnosis or prognosis information is desired. Gene expression monitoring is done on genes encoding Apop proteins. In one aspect, the expression levels of Apop genes are determined for different cellular states, such as normal cells and cells undergoing apoptosis. By comparing Apop gene expression levels in cells in different states, information including both up- and down-regulation of Apop genes is obtained, which can be used in a number of ways. For example, the evaluation of a particular treatment regime may be evaluated: does a chemotherapeutic drug act to improve the long-term prognosis in a particular patient. Similarly, diagnosis may be done or confirmed by comparing patient samples. Furthermore, these gene expression levels allow screening of drug candidates with an eye to mimicking or altering a particular expression level. This may be done by making biochips comprising sets of important Apop genes, such as those of the present invention, which can then be used in these screens. These methods can also be done on the protein basis; that is, protein expression levels of the Apop proteins can be evaluated for diagnostic purposes or to screen candidate agents. In addition, the Apop nucleic acid sequences can be administered for gene therapy purposes, including the administration of antisense nucleic acids, or the Apop proteins administered as therapeutic drugs.

Apop sequences bound to biochips include both nucleic acid and amino acid sequences as defined above. In a preferred embodiment, nucleic acid probes to Apop nucleic acids (both the nucleic acid sequences having the sequences outlined in FIGS. 1, 3, and 5 (SEQ ID NOS:1, 3 & 5) and/or the complements thereof) are made. The nucleic acid probes attached to the biochip are designed to be substantially complementary to the Apop nucleic acids, i.e. the target sequence (either the target sequence of the sample or to other probe sequences, for example in sandwich assays), such that hybridization of the target sequence and the probes of the present invention occurs. As outlined below, this complementary need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A "nucleic acid probe" is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 based being particularly preferred. In some embodiments, much longer nucleic acids can be used, up to hundreds of bases (e.g., whole genes).

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably show fluorescence.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155-200, incorporated herein by reference). In addition, in some cases, additional linkers, such as alkyl groups (including substituted and heteroalkyl groups) may be used.

In this embodiment, oligonucleotides, corresponding to the nucleic acid probe, are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix GeneChip™ technology.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, normal versus apoptotic cell. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, Nature Biotechnology 14:1675-1680 (1996), hereby expressly incorporated by reference. Other techniques include, but are not limited to, quantitative reverse transcriptase PCR, Northern analysis and RNase protection.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or alternatively, the final gene product itself (protein) can be monitored, for example through the use of antibodies to the Apop protein and standard immunoassays (ELISAs, etc.) or other techniques, including mass spectroscopy assays, 2D gel electrophoresis assays, etc.

In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the m RNA encoding an Apop protein is detected by binding the digoxygenin with an anti-digoxygenin secondary antibody and developed with nitro blue tetrazolium and 5-bromo-4-chloro-3-indoyl phosphate.

In another preferred method, expression of Apop proteins is performed using in situ imaging techniques employing antibodies to Apop proteins. In this method cells are contacted with from one to many antibodies to the Apop protein(s). Following washing to remove non-specific antibody binding, the presence of the antibody or antibodies is detected. In one embodiment the antibody is detected by incubating with a secondary antibody that contains a detectable label. In another method the primary antibody to the Apop protein(s) contains a detectable label. In another preferred embodiment each one of multiple primary antibodies contains a distinct and detectable label. This method finds particular use in simultaneous screening for a plurality of Apop proteins. The label may be detected in a fluorometer which has the ability to detect and distinguish emissions of different wavelengths. In addition, a fluorescence activated cell sorter (FACS) can be used in this method. As will be appreciated by one of ordinary skill in the art, numerous other histological imaging techniques are useful in the invention and the antibodies can be used in ELISA, immunoblotting (Western blotting), immunoprecipitation, BIA-CORE technology, and the like.

In one embodiment, a therapeutically effective dose of an Apop is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for Apop degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the Apop proteins of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the Apop may be directly applied as a solution or spray.

The pharmaceutical compositions of the present invention comprise an Apop protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; filters such as microcrystalline cellulose, lactose, corn and other starches; binding agents; sweeteners and other flavoring agents; coloring agents; and polyethylene glycol. Additives are well known in the art, and are used in a variety of formulations.

In another preferred embodiment, antisense RNAs and DNAs can be used as therapeutic agents for blocking the expression of Apop genes in vivo. The term "antisense" herein means that the nucleic acid sequence of the antisense RNA or DNA comprises the reverse complement sequence of the mRNA to which it can bind. For example, if the mRNA, whose expression (i.e., translation into a protein) is to be blocked, comprises the nucleic acid sequence 5'-GGAAUUGGAGC-3' (SEQ ID NO:7), then the antisense RNA comprises the nucleic acid sequence of 5'-GCUC- CAAUUCC-3' (SEQ ID NO:8) and the antisense DNA comprises the nucleic acid sequence of 5'-GCTCCAAT-TCC-3' (SEQ ID NO:9).

An Apop antisense molecule as defined herein is a nucleic acid molecule which exhibits at least 75%, more preferably at least 80%, even more preferably at least 90%, and most preferably more than at least 95% reverse-complement identity to its target sequence. In one embodiment herein, an Apop antisense molecule exhibits 100% reverse-complement identity to its target sequence. As known in the art, the antisense nucleic acid can comprise nucleotide homologues, such as inosine, etc.

An Apop antisense molecule as defined herein is a nucleic acid molecule which inhibits expression or translation of an Apop nucleic acid by at least 30%, preferably by at least 40%, more preferably by at least 50%, even more preferably by at least 70%, and most preferably by at least 90%. In one embodiment herein, an Apop antisense molecule inhibits expression or translation of mRNA encoding Apop 100%.

Generally, the Apop antisense molecule is at least about 10 nucleotides in length, more preferably at least 12, and most preferably at least 15 nucleotides in length. The skilled artisan understands that the length can extend from 10 nucleotides or more to any length which does not inhibit binding to the Apop nucleic acid. In a preferred embodiment herein, the length is about 100 nucleotides long, more preferably about 50 nucleotides, more preferably about 25 nucleotides, and most preferably about 12 to 25 nucleotides in length.

It has already been shown that short antisense oligonucleotides can be imported into cells where they act as inhibitors, despite their low intracellular concentrations caused by their restricted uptake by the cell membrane [Zamecnik et al., Proc. Natl. Acad. Sci. U.S.A. 83:4143-4146 (1986)]. The oligonucleotides can be modified to enhance their uptake, e.g. by substituting their negatively charged phosphodiester groups by uncharged groups. There are a variety of techniques available for introducing nucleic acids into viable cells. The techniques vary depending upon whether the nucleic acid is transferred into cultured cells invitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The current preferred in vivo gene transfer techniques include transfection with viral (typically retroviral) vectors and viral coat protein-liposome mediated transfection [Dzau et al., Trends in Biotechnology 11:205-210 (1993)]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262:4429-4432 (1987); and Wagner et al., Proc. Natl. Acad. Sci. U.S.A. 87:3410-3414 (1990). For review of gene marking and gene therapy protocols see Andersen et al., Science 256:808-813 (1992).

In a preferred embodiment, the Apop proteins of the present inventions are used as "bait proteins" in a yeast two-hybride screening or in a mammalian two-hybrid screening (Luo et al., Biotechniques 22:350-352 (1997) and U.S. application Ser. No. 09/050,863, both of which are expressly incorporated as references in their entirety) to isolate novel proteins interacting with the Apop proteins.

The following examples serve to move fully describe the manner of using above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLE 1

Isolation and Sequence Analysis of Apop3

Several known TNFα signaling proteins have been shown in bind RIP [Hsu et al., Immunity 4:387-396 (1996)] and complexes formed by the interactions between RIP kinase, TRADD, FADD, and RAIDD recruit other proteins to TNFR1 or Fas receptors to initiate signaling [Stanger et al., Cell 81:513-523 (1995); Hsu et al., Immunity 4:387-396 (1996); Tartaglia et al., Cell 74:845-853 (1993); Darnay et al., J. Leukoc, Biol. 61:559-566 (1997); Askhenazi and Dixit, Science 281:1305-1308 (1998)]. We established a large-scale yeast two hybrid screening system designed to isolate rare mRNAs and verify novel protein-protein interactions involved in the TNF signaling pathway. Using RIP as bait, we screened 96 million independent yeast transformants with a combined Hela/Lymphocyte cDNA library in a single transformation round. As expected, many of the known RIP binding proteins, including TRAF1, TRAF2, TNFR1, RIP, TRADD, and FADD, were cloned; several novel genes were isolated as well. One of the novel cDNAs had high sequence homology with RIP. The full-length cDNA (FIG. 5; SEQ ID NO:5) contains a 518 amino acid open reading frame, encoding a protein designated Apop3. Analysis of the amino acid sequence of this novel protein (FIG. 6; SEQ ID NO:6) revealed a kinase domain (aa 21-287) which had 47% homology to the kinase domain of RIP and 42% homology to that of RIP2/Rick/CARDIAK. However, outside the kinase domain, the C-terminal region of Apop3 had no homology to death domains [Tartaglia et al., Cell 74:845-853 (1993)], death effector domains [Siegel et al., J. Cell. Biol. 141:1243-1253 (1998)], or the CARD region [Hofmann et al., Trends Biochem. Sci. 22:155-156 (1997)]. An approximately 2.1 Kb transcript was detected with a cDNA probe specific to Apop3 in both normal human tissue and human tumor RNA blots (data not shown).

EXAMPLE 2

Co-Immunoprecipitaton with Apop3 and Other Members of TNFα Signaling Complex

We confirmed the association of Apop3 and other members of TNFα signaling complex in mammalian cells by co-immunoprecipitation. To further analyze which region of Apop3 was important for interactions with RIP, a series of deletion mutants were engineered (FIG. 7). In yeast, the intermediate region (aa 82-436) of Apop3 was required for the interaction between RIP and Apop3 (FIG. 8). Co-immunoprecipitation analysis was performed to verify the interaction of RIP with Apop3 by co-transfection of HA-tagged RIP with the Flag-tagged full length and truncated mutants of Apop3 in Phoenix-A (293 T) cells. In this example, cell lysates were collected from Phoenix-A cells 24 hours after the co-transfection of HA-RIP (5 μg) with a Flag-control protein or with one of the Flag-Apop3 proteins, schematically depicted in FIG. 7 (5 μg). Co-precipitated Flag-Apop3 proteins were detected by immunoblotting with anti-Flag polyclonal Ab. The full length Apop3 co-immunoprecipitated with RIP, as well as Apop3(82-518) and Apop3(K50D) mutants (data not shown). Interestingly, the Apop3(1-436) mutant has dramatically reduced binding affinity for RIP. No association was detected between RIP and Apop3(1-251), Apop3(1-196), or Apop3(287-518). This suggests that the interaction between Apop3 and RIP is mediated by a portion of the kinase domain with contribution from the carboxyl-domain of Apop3.

EXAMPLE 3

Apop3 Binds to Endogenous RIP

To test whether Apop3 was able to bind to endogenous RIP, Flag-Apop3 was transfected into Phoenix-A (293 T) cells in the presence and absence of TNFα stimulation. In this example, 293 T cells were transfected with Flag-control protein, and Flag-Apop3 ( 10 μg). After 18 hours incubation, cells were treated with or without 20 ng/ml huTNFα for 6 hours. The cell extracts were harvested 24 hours after transfection. The immunoprecipitated proteins were immunoblotted with goat anti-RIP polyclonal Ab. Ectopically expressed Apop3 was able to bind to endogenous RIP kinase (data not shown). TNFα treatment did not significantly affect this binding (data not shown).

EXAMPLE 4

Endogenous Apop3 Bins to TRAF2 and TNFR1

In addition, endogenous TNFR1 was co-immunoprecipitated with ectopically expressed Apop3 and endogenous Apop3 was co-immunoprecipitated with ectopically expressed TRAF2 (data not shown). Interaction between TRAF2 and Apop3 was also verified by the yeast two-hybrid system (data not shown). This suggests that Apop3 is part of the TNFR1 signaling complex. In this example, Flag-tagged TRAF2 expression vector was transfected into cells. Association with endogenous Apop3 was detected by anti-Apop3 Ab. Further, Flag-tagged Apop3 was transfected into cells ans association with endogenous TNFR1 was detected by anti-TNFR1 Ab (data not shown).

EXAMPLE 5

Demonstration of APOP3 Kinase Activity

Apop3 contains consensus Ser/Thr kinase motifs. The lysine 50 of the Apop3 kinase domain, homologous to the conserved lysine in RIP and critical enzymatic activity and ATP-binding [McCarthy et al., J. Biol. Chem. 273:16968-16975 (1998); Inohara et al., J. Bio. Chem. 273:12296-12300 (1998)], was substituted with aspartic acid. An in vitro kinase assay demonstrated that Apop3 was a kinase and was autophosphorylated (data not shown). However, the Apop3)K50D) mutant lost the kinase activity (data not shown), suggesting that this lysine is required for autophosphorylation. In this example, Phoenix-A cells were transfected with 10 μg of a Flag-vector, Flag-Apop3 and Flag-Apop3(K50D), respectively. The lysates were immunoblotted with anti-Flag mAb to adjust protein amount for IP.

EXAMPLE 6

Induction of Cell Death by Apop3

To test whether Apop3 was able to induce cell death, Phoenix-A cells were co-transfected with a eukaryotic expression vector encoding Apop3 and a pGDB control for transfection efficiency [Xu et al., Nucl. Acids Res. 26:2034-2035 (1998)]. The GFP-positive Apop3-transfected cells displayed morphological characteristics of apoptosis, including detachment from the plate substrate and resultant "rounding up" and a condensed/fragmented nucleus [Cryns et al., Cell 82:349-352 (1995)] (data not shown). The C-terminal deletion mutant, Apop3(1-436), failed to induce apoptosis. Apop3-induced apoptosis was also observed in Hela cells (data not shown). FIG. 9 shows approximately 35% cell death in the Apop3 transfected Phoenix-A cells, compared with only 2% apoptosis in cells transfected with control vector. Similar to RIP [Hsu et al., Immunity 4:387-396 (1996)] and RIP2/Rick/CRDIAK kinase deletions [McCarthy et al., J. Biol. Chem. 273:16968-16975 (1998)], the deletion of the Apop3 kinase domain had no effect on its pro-apoptotic activity (data not shown), which suggested the kinase domain was not required for Apop3-mediated cell death.

EXAMPLE 7

Activation of Cellular Caspases by Apop3

TNFα and Fas ligand induced apoptosis is controlled by caspase activation [Martin and Green, Cell 82:349-352 (1995)]. Rick/RIP2/CARDIAK kinase has also been reported to induce apoptosis through enhancement of caspase activity [Inohara et al., J. Bio. Chem. 273:12296-12300 (1998)]. To test whether Apop3 activates cellular caspases, pYCI-Apop3 (data not shown) was co-transfected into Phoenix-A cells with pGDB. In this example, $2 \times 10^6$ Phoenix-A cells were co-transfected with expression vectors encoding Apop3 and Apop3 mutants, such as depicted in FIG. 7 (10 μg) with pGDB (3 μg). Lysates were analyzed by Western blot probed with anti-GFP monoclonal antibodies. Caspase cleavage released the monomeric GFP as indicated by the arrow. pGDB expresses a previously described BFP-GFP hybrid protein linked by a DEVD containing peptide ('GFP'-GSGSGSDEVDGGSGSGS-'BFP' (SEQ ID NO:10), wherein the caspase cleavage site is in between V and D) used as a reporter of intracellular caspase activity [Xu et al., Nucl. Acids Res. 26:2034-2035 (1998)]. When caspases 2, 3, or 7 are activated, they specifically cleave appropriately accessible substrates at the DEVD peptide [Cryns et al., Cell 82:349-352 (1995)] and release GFP/BFP monomers. Western blot analysis using anti-GFP monoclonal antibody indicated that ectopic expression of Apop3 activated caspases to cleave the DEVD linker peptide, releasing GFP/BFP monomer (data not shown). A broad-spectrum inhibitor of caspases, zVAD-fmk [Zhu et al., FEBS Lett. 374:303-308 (1995)], inhibited the caspase activity triggered by Apop3 expression (data not shown). This result confirmed that the cleavage of the chimeric protein was due to caspase activation (data not shown). Apop3-induced apoptosis could also be inhibited by CrmA (data not shown). N-terminal deletion mutants Apop3(82-518), Apop3(287-518) and Apop3(K50D) were still able to activate the caspase activity (data not shown). Deletion of the C-terminal region of Apop3, Apop3)1-251) and Apop3(1-436), completely abrogated caspase activation (data not shown). These results indicate again that Apop3's kinase activity is not required for activation of caspases and cell death. Since the C-terminal domain (aa 437-518) of Apop3 is not required for the binding of Apop3 to RIP, this region may be involved in binding to other proteins involved in novel signaling pathway(s) leading to apoptosis. It is not known whether the C-terminal region of Apop3 is able to bind directly to known death adaptor or death protease. Additional two-hybrid screening using Apop3 as bait is being carried out to find signaling proteins downstream of Apop3.

EXAMPLE 8

Induction of Activation of NFκB by Apop3

We also tested whether Apop3 could induce NFκB activation. Phoenix-A cells were harvested for a luciferase reporter assay 24 hours after co-transfection with an NFκB-dependent luciferase reporter construct and an Apop3 expression vector (pYCI-Apop3; data not shown). Ectopic expression of Apop3 alone induced NFκB activation approximately 7 fold (FIG. 10 and data not shown). The NFκB activation could be inhibited by co-transfection of a IκB dominant negative mutant (data not shown). The C-terminal region was essential for NFκB activation, Apop3(1-251) and Apop3(1-436) were not able to activate NFκB (FIG. 10). Interestingly, Apop3(K50D), Apop3(82-518), and Apop3(287-518) induced higher luciferase activity than full length Apop3 (FIG. 10). This suggests that the kinase domain of Apop3 is not required for the NFκB activation. In contrast, Apop3 had no noticeable effect on AP-1 activation pathways (data not shown).

EXAMPLE 9

Overexpression of Apop3 Inhibits TNFα-Induced Caspase Activation but not TNFα-Induced NFκB Activation Although Apop3 associates with RIP and TRAF2 and activates apoptosis and NFκB, its function in the TNFα signaling pathway needs to be dissected. In this example, Phoenix-A (293 T) cells were co-transfected with expression vectors encoding Apop3 and Apop3 mutants, such as depicted in FIG. 7 (3 μg) with pGDB (0.3 μg) and RIP (0.1 μg). After 24 hours of transfection, cell lysates were harvested and analyzed by Western blot analysis with anti-GFP monoclonal antibodies. In these experiments, Apop3(1-436) inhibited TNFα-induced caspase activation (data not shown) but not TNFα-induced NFκB activation (data not shown), suggesting that Apop3 is involved in the TNFα-mediated apoptosis pathway. These results imply that without the C-terminal domain (aa 437-518), Apop3 either competes with or fails to recruit other proteins of the TNF signaling of a complex required for the activation of caspases. In separate experiments, Apop3)1-436) was able to down-regulate RIP-mediated apoptosis activation (data not shown). Co-transfection of full length of Apop3 (3 μg) with RIP (0.1 μg) resulted in greater caspase activity than with RIP alone (data not shown). However, Apop3(1-436) significantly reduced RIP-induced caspase activity (data not shown). On the other hand, although Apop3 alone was able to activate NFκB, co-transfection of RIP (0.3 μg) and full length Apop3 (3 μg) in Phoenix cells did not show any synergistic effect on NFκB activation (data not shown). When Apop3(1-436) was co-transfected with RIP, it only slightly reduced RIP-mediated NFκB activation (data not shown). Another Apop3 mutant (aa 287-518) was still able to activate caspase and NFκB, even though it did not bind to RIP (data not shown).

In summary, we demonstrated that Apop3 is a novel kinase associated with the TNFα signaling complex. Apop3 binds to RIP and TRAF2 in both yeast and mammalian cells and co-immunoprecipitates with TNFR1. Although RIP is essential player in TNFα induced NFκB activation [Keliher et al., Immunity 8:297-303 (1998)] and Apop3 was cloned by binding to RIP, the function of Apop3 may not rely solely on its binding to RIP. A dominant negative form of Apop3 is able to inhibit TNFα-induced caspase activation without affecting TNFα-induced NFκB activation, suggesting that Apop3 may be involved in TNFα-induced apoptosis. It is possible that Apop3 and RIP are therefore involved in two different areas of TNFα signaling; apoptosis and NFκB activation, respectively. The precise role of Apop3 in TNFα signaling may be answered by future knock-out experiments.

EXAMPLE 10

The Yeast Two-Hybrid Screening Method: Plasmids, cDNA Libraries, Yeast Strains, Growth Media and Retrieval of Plasmids Unknown protein interacting with a known "Bait" protein can be identified using the yeast two-hybrid screening method. In this method, a known "Bait" protein (such as XIAP or RIP) is encoded on a "bait vector" and a protein (the "Test" protein) which may bind to the "Bait" protein is usually encoded on a "test" vector or "test" plasmid. The method comprises the following steps: (1) transforming yeast with a "bait" vector and a "test" vector (usually a library); (2) detecting an interaction between the bait protein and a test protein (usually by expression of a reporter gene such as IacZ); (3) growing the identified yeast colony; (4) isolating the "test" vector; (5) transforming the "test" vector into *E.coli*; and (6) using standard techniques to further characterize the "test" vector and the encoded "test" protein.

Plasmids and cDNA Libraries: The pAS2 and pACT2 plasmid series were originally constructed by Elledge and co-workers [Durfee et al., Genes Dev. 4:555-59 (1993)]. The bait vector used in our screening is either pAS2 or pAS2K. pAS2K was constructed by replacing the $Amp^R$ gene in pAS2 with a $Kan^R$ gene. cDNA libraries used in our screening were made, e.g., either from brain tissues or T and B lymphocytes.

The yeast two-hybrid system reporter strain Y190 (MATa, ura3-52, his3-200, lys2-801, ade2-101, trp1-901, leu2-3, 112, gal4D, gal80D, cyhr2, LYS2::GAL1UAS-HIS3TATA-HIS3, URA3::GAL1UAS-GAL1TATA-lacZ) was used in all screenings.

All yeast culture mediums, including, e.g., YPD, YPD Agar, DOB, DOBA, CSM-TRP, CSM-LEU, CSM-HIS, CSM-URA, CSM-LYS, CSM-LEU-TRP, CSM-LEU-HIS, and CSM-LEU-TRP-HIS, are available from Bio101, Inc. 3AT (3-amino-1,2,4-triazol) is available from Sigma (Cat#A-8056, St. Louis, Mo. USA).

There are several methods to retrieve plasmids from yeast, ranging from lyticase lysis to glass beads.

The glass beads method is listed below:

1. Inoculate 3 ml of selection medium (e.g., SD-L for cDNA library plasmid pACT) with a yeast colony.

2. Incubate in a 30° C. shaker or rotator overnight or until confluent.

3. Spin down yeast in a bench-top centrifuge at 3000 rpm at room temperature.

4. Remove medium and re-suspend pellet in 200 μl lysis buffer. Transfer to an eppendorf tube.

5. Add 200 μl volume glass beads.

6. Add 200 μl phenol/chloroform/isoamyl alcohol (25:24:1).

7. Vortex at the highest speed for 3 minutes.

8. Spin in micro-centrifuge at 14000 rpm for 10 minutes.

9. Transfer top water layer to another eppendor tube, add 20 μl 3M NaAc and 500 μl ethanol.

10. Put the eppendorf tube into a dry ice bath for 15 minutes or until frozen.

11. Spin in a micro-centrifuge 14000 rpm for 10 minutes.

12. Remove supernatant and dry pellet.

13. Wash pellet by 100 μl of 80% ethanol, and dry the pellet in air.

14. Re-suspend pellet in 30 μl $H_2O$ and use 1 μl for electroportion to transform *E. coli*.

Electroporation method is by far the most efficient method to transform plasmids from yeast miniprep into *E. coli*. Bait and cDNA (test) plasmids may carry different antibiotic selection markers to facilitate separation in *E. coli*. For example, our bait plasmid carriers a $Kan^R$ gene and the cDNA (test) plasmid carriers an $Amp^R$ gene.

We claim:

1. A recombinant nucleic acid encoding an Apop3 protein that comprises an amino acid sequence at least 85% identical to the amino acid sequence depicted in FIG. 6 (SEQ ID NO:6), wherein the Apop3 protein induces apoptosis.

2. A recombinant nucleic acid according to claim 1 comprising the nucleotide sequence depicted in FIG. 5 (SEQ ID NO:5) or its full complement.

3. A recombinant nucleic acid according to claim 1 wherein said nucleic acid hybridizes under high stringency conditions to the full complement of the nucleotide sequences depicted in FIG. 5 (SEQ ID NO:5) or its complement, wherein the hybridization takes place at 60° C. in the presence of between 0.01 M and 1.0 M sodium ion, and at a pH between 7.0 and 8.3.

4. A recombinant nucleic acid according to claim 1 wherein said nucleic acid comprises a nucleotide sequence at least 85% identical to the nucleotide sequence depicted in FIG. 5 (SEQ ID NO:5) or its full complement.

5. A recombinant nucleic acid according to claim 1 wherein said Apop3 protein comprises the amino acid sequence depicted in FIG. 6 (SEQ ID NO:6).

6. A recombinant nucleic acid comprising nucleotide 1-822 depicted in FIG. 5 (SEQ ID NO:5), or its full complement.

7. A recombinant nucleic acid according to claim 1 operably linked to control sequences recognized by a host cell transformed with the nucleic acid.

8. An expression vector comprising the nucleic acid of claim 1.

9. An isolated host cell comprising the nucleic acid of claim 1.

10. An isolated host cell comprising the expression vector of claim 8.

11. A recombinant Apop3 protein comprising an amino acid sequence at least 85% identical to the amino acid sequence depicted in FIG. 6 (SEQ ID NO:6), wherein the Apop3 protein induces apoptosis.

12. An Apop3 protein according to claim 11 comprising the amino acid sequence depicted in FIG. 6 (SEQ ID NO:6).

13. An Apop3 protein according to claim 11 wherein said Apop3 protein is encoded by a nucleic acid comprising the nucleotide sequence depicted in FIG. 5 (SEQ ID NO:5) or its full complement.

14. An Apop3 protein according to claim 11 wherein said Apop3 protein is encoded by a nucleic acid which nucleic acid comprises a nucleotide sequence at least 85% identical to the nucleotide sequence depicted in FIG. 5 (SEQ ID NO:5) or its full complement.

15. An Apop3 protein according to claim 11 wherein said Apop3 protein is encoded by a nucleic acid which nucleic acid will hybridize under high stringency conditions to the full complement of the nucleotide sequence depicted in FIG. 5 (SEQ ID NO:5) or its complement, wherein the hybridization takes place at 60° C. in the presence of between 0.01 M and 1.0 M sodium ion, and at a pH between 7.0 and 8.3.

16. A recombinant Apop3 protein comprising the amino acid sequence 1-274 depicted in FIG. 6 (SEQ ID NO:6), wherein the Apop3 protein induces apoptosis.

17. A process for producing an Apop3 protein according to claim 11 comprising culturing the host cell of claim 10 under conditions suitable for expression of said Apop3 protein.

18. A process according to claim 17, further comprising recovering said Apop3 protein.

19. A method for screening for a bioactive agent capable of modulating the apopiotic activity of an Apop3 protein according to claim 11, said method comprising the steps of:

a) adding a candidate bioactive agents to a cell comprising a recombinant nucleic acid encoding said Apop3 protein, wherein said Apop3 protein induces apoptosis; and b) determining the effect of the candidate bioactive agent on apoptosis, thereby determining the ability of the candidate bioactive agent to modulate the apopiotic activity of the Apop3 protein.

20. A method according to claim 19 wherein a library of candidate bioactive agents is added to a plurality of cells comprising a recombinant nucleic acid encoding said Apop3 protein.

21. The recombinant nucleic acid according to claim 1 wherein said nucleic acid comprises a nucleotide sequence at least 90% identical to the nucleotide sequence depicted in FIG. 5 (SEQ ID NO:5) or its full complement.

22. The recombinant nucleic acid according to claim 1 wherein said nucleic acid comprises a nucleotide sequence at least 95% identical to the nucleotide sequence depicted in FIG. 5 (SEQ ID NO:5) or its full complement.

23. The Apop3 protein according to claim 11, comprising an amino acid sequence at least 90% identical to SEQ ID NO:6.

24. The Apop3 protein according to claim 11, comprising an amino acid sequence at least 95% identical to SEQ ID NO:6.

* * * * *

SEQUENCE LISTING

```
<160> NUMBER OF SEQ ID NOS: 10

<210> SEQ ID NO 1
<211> LENGTH: 1155
<212> TYPE: DNA
<213> ORGANISM: Homo sapiens

<400> SEQUENCE: 1
cacagacagg ctcttaactg tttatatcac tcacttggga aagtgtctca agctgttcta      60
caaatccatg caaaggccgt ttaaaaatag cagcgaaggt cctggactcg gtctcgtcca     120
gcacagcccc ttggctctct ctctgggctc tggccgcctg gccccgggg acccacacga     180 ggtcatggcg tgcttcgggc agggggggcgg ggatcccata gacacctcag ctccttaaga    240
```

-continued

```
gttctccgcc tgggccagga cgagcatggg ggtccccact gatgcccgag acagtgcccc    300
tgtgtgtgtg agccctcgac ccacataaca gagaggtgtc ctgatgccct ctgtcctctc    360
caggtggatc taggatccgg cttccaacat gtggcagctc tgggcctccc tctgctgcct    420
gctggtgttg gccaatgccc ggagcaggcc ctctttccat cccgtgtcgg atgagctggt    480
caactatgtc aacaaacgga ataccacgtg gcaggccggg cacaacttct acaacgtgga    540
catgagctac ttgaagaggc tatgtggtac cttcctgggt gggcccaagc caccccagag    600
agttatgttt accgaggacc tgaagctgcc tgcaagcttc gatgcacggg aacaatggcc    660
acagtgtccc accatcaaag agatcagaga ccagggctcc tgtggctcct gctgggtaag    720
gccctgctgg ctggtgggga agcgctggag agaaagtggg agcaacactg gagagtcttg    780
ggggattcgg ggtggggaca actctgacaa ggcaagttat agaaactttc tgagtcccag    840
tttccatcag tacaaaaatc acaatccctc tggccatgaa tgatggcgag gattaggtgg    900
agtggcgggc agagcatcca gcagattgca agtccacgtg tacaggtggc gaagcagctc    960
cctttccctg acatgctggc ccgtccgcaa ataccaggag ctctcactgc tactctgctt   1020
caagaaagca tcccttagt gtcagtgagc tgtcttaatt ttgtcattta attgtggtaa   1080
aatacacgta acagaaatgt aataatctta gcaatcttct tttgttttct ttctttt     1140
tttttttttt ttttt                                                    1155
```

<210> SEQ ID NO 2
<211> LENGTH: 164
<212> TYPE: PRT
<213> ORGANISM: Homo sapiens

<400> SEQUENCE: 2

```
Met Trp Gln Leu Trp Ala Ser Leu Cys Cys Leu Leu Val Leu Ala Asn
1               5                   10                  15

Ala Arg Ser Arg Pro Ser Phe His Pro Val Ser Asp Glu Leu Val Asn
            20                  25                  30

Tyr Val Asn Lys Arg Asn Thr Thr Trp Gln Ala Gly His Asn Phe Tyr
        35                  40                  45

Asn Val Asp Met Ser Tyr Leu Lys Arg Leu Cys Gly Thr Phe Leu Gly
    50                  55                  60

Gly Pro Lys Pro Gln Arg Val Met Phe Thr Glu Asp Leu Lys Leu
65                  70                  75                  80

Pro Ala Ser Phe Asp Ala Arg Glu Gln Trp Pro Gln Cys Pro Thr Ile
                85                  90                  95

Lys Glu Ile Arg Asp Gln Gly Ser Cys Gly Ser Cys Trp Val Arg Pro
            100                 105                 110

Cys Trp Leu Val Gly Lys Arg Trp Arg Glu Ser Gly Ser Asn Thr Gly
        115                 120                 125

Glu Ser Trp Gly Ile Arg Gly Gly Asp Asn Ser Asp Lys Ala Ser Tyr
    130                 135                 140

Arg Asn Phe Leu Ser Pro Ser Phe His Gln Tyr Lys Asn His Asn Pro
145                 150                 155                 160

Ser Gly His Glu
```

<210> SEQ ID NO 3
<211> LENGTH: 1294
<212> TYPE: DNA
<213> ORGANISM: Homo sapiens

```
<400> SEQUENCE: 3
tccaagtcct ggatgagctc ggaagacacg tgctgctgcg aaggactgt ggcccagtgg      60 acaccaaggt tccaggtgct ggggagccca agtcagcctt cactcagggc tcagccatga     120
tttcttctct gtcccaaaac catccagaca acagaaacga gactttcagc tcagtcattt     180
ccctgttgaa tgaggatccc ctgtcccagg acttgcctgt gaagatggct tcaatcttca     240
agaactttgt cattacctat aaccggacat atgagtcaaa ggaagaagcc cggtggcgcc     300
tgtccgtctt tgtcaataac atggtgcgag cacagaagat ccaggccctg gaccgtggca     360
cagctcagta tggagtcacc aagttcagtg atctcacaga ggaggagttc cgcactatct     420
acctgaatac tctcctgagg aaagagcctg gcaacaagat gaagcaagcc aagtctgtgg     480
gtgacctcgc cccacctgaa tgggactgga ggagtaaggg ggctgtcaca aaagtcaaag     540
accagggcat gtgtggctcc tgctgggcct tctcagtcac aggcaatgtg gagggccagt     600
ggtttctcaa ccaggggacc ctgctctccc tctctgaaca ggagctcttg gactgtgaca     660
agatggacaa ggcctgcatg ggcggcttgc cctccaatgc ctactcggcc ataaagaatt     720
tgggagggct ggagacagag gatgactaca gctaccaggg tcacatgcag tcctgcaact     780
tctcagcaga aaggccaag gtctacatca tgactccgt ggagctgagc cagaacgagc     840
agaagctggc agcctggctg ccaagagag gcccaatctc cgtggccatc aatgcctttg     900
gcatgcagtt ttaccgccac gggatctccc gccctctccg gcccctctgc agcccttggc     960
tcattgacca tgcggtgttg cttgtgggct acggcaaccg ctctgacgtt ccctttttggg    1020 ccatcaagaa cagctggggc actgactggg gtgagaaggg ttactactac ttgcatcgcg    1080
ggtccggggc ctgtggcgtg aacaccatgg ccagctcggc ggtggtggac tgaagagggg    1140
cccccagctc gggacctggt gctgatcaga gtggctgctg ccccagcctg acatgtgtcc    1200
aggcccctcc ccgggaggta cagctggcag agggaaaggc actgggtacc tcagggtgag    1260
cagagggcac tgggctgggg cacagcccct gctt                               1294

<210> SEQ ID NO 4
<211> LENGTH: 338
<212> TYPE: PRT
<213> ORGANISM: Homo sapiens

<400> SEQUENCE: 4

Met Ile Ser Ser Leu Ser Gln Asn His Pro Asp Asn Arg Asn Glu Thr
1               5                   10                  15

Phe Ser Ser Val Ile Ser Leu Leu Asn Glu Asp Pro Leu Ser Gln Asp
            20                  25                  30

Leu Pro Val Lys Met Ala Ser Ile Phe Lys Asn Phe Val Ile Thr Tyr
        35                  40                  45

Asn Arg Thr Tyr Glu Ser Lys Glu Glu Ala Arg Trp Arg Leu Ser Val
    50                  55                  60

Phe Val Asn Asn Met Val Arg Ala Gln Lys Ile Gln Ala Leu Asp Arg
65                  70                  75                  80

Gly Thr Ala Gln Tyr Gly Val Thr Lys Phe Ser Asp Leu Thr Glu Glu
                85                  90                  95

Glu Phe Arg Thr Ile Tyr Leu Asn Thr Leu Leu Arg Lys Glu Pro Gly
            100                 105                 110

Asn Lys Met Lys Gln Ala Lys Ser Val Gly Asp Leu Ala Pro Pro Glu
        115                 120                 125

Trp Asp Trp Arg Ser Lys Gly Ala Val Thr Lys Val Lys Asp Gln Gly
```

-continued

```
                130                 135                 140
Met Cys Gly Ser Cys Trp Ala Phe Ser Val Thr Gly Asn Val Glu Gly
145                 150                 155                 160

Gln Trp Phe Leu Asn Gln Gly Thr Leu Leu Ser Leu Ser Glu Gln Glu
                165                 170                 175

Leu Leu Asp Cys Asp Lys Met Asp Lys Ala Cys Met Gly Gly Leu Pro
            180                 185                 190

Ser Asn Ala Tyr Ser Ala Ile Lys Asn Leu Gly Gly Leu Glu Thr Glu
        195                 200                 205

Asp Asp Tyr Ser Tyr Gln Gly His Met Gln Ser Cys Asn Phe Ser Ala
210                 215                 220

Glu Lys Ala Lys Val Tyr Ile Asn Asp Ser Val Glu Leu Ser Gln Asn
225                 230                 235                 240

Glu Gln Lys Leu Ala Ala Trp Leu Ala Lys Arg Gly Pro Ile Ser Val
                245                 250                 255

Ala Ile Asn Ala Phe Gly Met Gln Phe Tyr Arg His Gly Ile Ser Arg
            260                 265                 270

Pro Leu Arg Pro Leu Cys Ser Pro Trp Leu Ile Asp His Ala Val Leu
        275                 280                 285

Leu Val Gly Tyr Gly Asn Arg Ser Asp Val Pro Phe Trp Ala Ile Lys
290                 295                 300

Asn Ser Trp Gly Thr Asp Trp Gly Glu Lys Gly Tyr Tyr Tyr Leu His
305                 310                 315                 320

Arg Gly Ser Gly Ala Cys Gly Val Asn Thr Met Ala Ser Ser Ala Val
                325                 330                 335

Val Asp
```

<210> SEQ ID NO 5
<211> LENGTH: 1557
<212> TYPE: DNA
<213> ORGANISM: Homo sapiens

<400> SEQUENCE: 5

```
atgtcgtgcg tcaagttatg gcccagcggt gcccccgccc ccttggtgtc catcgaggaa    60
ctggagaacc aggagctcgt cggcaaagac gggttcggca cagtgttccg ggcgcaacat   120
aggaagtggg gctacgatgt ggcggtcaag atcgtaaact cgaaggcgat atccagggag   180
gtcaaggcca tggcaagtct ggataacgaa ttcgtgtttg ccctagaagg ggttatcgag   240
aaggtgaact gggaccaaga tcccaagccg gctctggtga ctaaattcat ggagaacggc   300
tccctgtcgg gctgctgca gtcccagtgc cctcggccct ggccgctcct ttgccgcctg   360
ctgaaagaag tggtgcttgg gatgttttac ctgcacgacc agaacccggt gctcctgcac   420
cgggacctca agccatccaa cgtcctgccg gacccagagc tgcacgtcaa gctggcagat   480
tttggcctgt ccacatttca ggaggctcaa cagtcaggga cagggtccgg ggagccaggg   540
ggcaccctgg gctacttggc cccagaactg tttgttaacg taaaccggaa ggcctccaca   600
gccagtgacg tctacagctt cgggatccta atgtgggcag tgcttgctgg aagagaagtt   660
gagttgccaa ccgaaccatc actcgtgtac gaagcagtgt gcaacaggca gaaccggcct   720
tcattggctg agctgcccca agccgggcct gagactcccg gcttagaagg actgaaggag   780
ctaatgcagc tctgctggag cagtgagccc aaggacagac cctccttcca ggaatgccta   840
ccaaaaactg atgaagtctt ccagatggtg gagaacaata tgaatgctgc tgtctccacg   900
gtaaaggatt tcctgtctca gctcaagagc agcaatagga gattttctat cccagagtca   960
```

-continued

```
ggccaaggag ggacagaaat ggatggcttt aggagaacca tagaaaacca gcactctcgt    1020
aatgatgtca tggtttctga gtggctaaac aaactgaatc tagaggagcc tcccagctct    1080
gttcctaaaa aatgcccgag ccttaccaag aggagcaggg cacaagagga gcaggttcca    1140
caagcctgga cagcaggcac atcttcagat tcgatggccc aacctcccca gactccagag    1200
acctcaactt tcagaaacca gatgcccagc cctacctcaa ctggaacacc aagtcctgga    1260
ccccgaggga atcagggggc tgagagacaa ggcatgaact ggtcctgcag gaccccggag    1320
ccaaatccag taacagggcg accgctcgtt aacatataca actgctctgg ggtgcaagtt    1380
ggagacaaca actacttgac tatgcaacag acaactgcct tgcccacatg gggcttggca    1440
ccttcgggca aggggagggg cttgcagcac cccccaccag taggttcgca agaaggccct    1500
aaagatcctg aagcctggag caggccacag ggttggtata atcatagcgg gaaataa     1557
```

<210> SEQ ID NO 6
<211> LENGTH: 519
<212> TYPE: PRT
<213> ORGANISM: Homo sapiens

<400> SEQUENCE: 6

```
Met Ser Cys Val Lys Leu Trp Pro Ser Gly Ala Pro Ala Pro Leu Val
1               5                   10                  15

Ser Ile Glu Glu Leu Glu Asn Gln Glu Leu Val Gly Lys Asp Gly Phe
            20                  25                  30

Gly Thr Val Phe Arg Ala Gln His Arg Lys Trp Gly Tyr Asp Val Ala
        35                  40                  45

Val Lys Ile Val Asn Ser Lys Ala Ile Ser Arg Glu Val Lys Ala Met
    50                  55                  60

Ala Ser Leu Asp Asn Glu Phe Val Leu Arg Leu Glu Gly Val Ile Glu
65                  70                  75                  80

Lys Val Asn Trp Asp Gln Asp Pro Lys Pro Ala Leu Val Thr Lys Phe
                85                  90                  95

Met Glu Asn Gly Ser Leu Ser Gly Leu Leu Gln Ser Gln Cys Pro Arg
            100                 105                 110

Pro Trp Pro Leu Leu Cys Arg Leu Leu Lys Glu Val Val Leu Gly Met
        115                 120                 125

Phe Tyr Leu His Asp Gln Asn Pro Val Leu Leu His Arg Asp Leu Lys
    130                 135                 140

Pro Ser Asn Val Leu Pro Asp Pro Glu Leu His Val Lys Leu Ala Asp
145                 150                 155                 160

Phe Gly Leu Ser Thr Phe Gln Gly Gly Ser Gln Ser Gly Thr Gly Ser
                165                 170                 175

Gly Glu Pro Gly Gly Thr Leu Gly Tyr Leu Ala Pro Glu Leu Phe Val
            180                 185                 190

Asn Val Asn Arg Lys Ala Ser Thr Ala Ser Asp Val Tyr Ser Phe Gly
        195                 200                 205

Ile Leu Met Trp Ala Val Leu Ala Gly Arg Glu Val Glu Leu Pro Thr
    210                 215                 220

Glu Pro Ser Leu Val Tyr Glu Ala Val Cys Asn Arg Gln Asn Arg Pro
225                 230                 235                 240

Ser Leu Ala Glu Leu Pro Gln Ala Gly Pro Glu Thr Pro Gly Leu Glu
                245                 250                 255

Gly Leu Lys Glu Leu Met Gln Leu Cys Trp Ser Ser Glu Pro Lys Asp
            260                 265                 270
```

-continued

```
Arg Pro Ser Phe Gln Glu Cys Leu Pro Lys Thr Asp Glu Val Phe Gln
        275                 280                 285

Met Val Glu Asn Asn Met Asn Ala Ala Val Ser Thr Val Lys Asp Phe
    290                 295                 300

Leu Ser Gln Leu Lys Ser Ser Asn Arg Arg Phe Ser Ile Pro Glu Ser
305                 310                 315                 320

Gly Gln Gly Gly Thr Glu Met Asp Gly Phe Arg Arg Thr Ile Glu Asn
                325                 330                 335

Gln His Ser Arg Asn Asp Val Met Val Ser Glu Trp Leu Asn Lys Leu
            340                 345                 350

Asn Leu Glu Glu Pro Pro Ser Ser Val Pro Lys Lys Cys Pro Ser Leu
        355                 360                 365

Thr Lys Arg Ser Arg Ala Gln Glu Glu Gln Val Pro Gln Ala Trp Thr
    370                 375                 380

Ala Gly Thr Ser Ser Asp Ser Met Ala Gln Pro Gln Thr Pro Glu
385                 390                 395                 400

Thr Ser Thr Phe Arg Asn Gln Met Pro Ser Pro Thr Ser Thr Gly Thr
                405                 410                 415

Pro Ser Pro Gly Pro Arg Gly Asn Gln Gly Ala Glu Arg Gln Gly Met
            420                 425                 430

Asn Trp Ser Cys Arg Thr Pro Glu Pro Asn Pro Val Thr Gly Arg Pro
        435                 440                 445

Leu Val Asn Ile Tyr Asn Cys Ser Gly Val Gln Val Gly Asp Asn Asn
450                 455                 460

Tyr Leu Thr Met Gln Gln Thr Thr Ala Leu Pro Thr Trp Gly Leu Ala
465                 470                 475                 480

Pro Ser Gly Lys Gly Arg Gly Leu Gln His Pro Pro Val Gly Ser
                485                 490                 495

Gln Glu Gly Pro Lys Asp Pro Glu Ala Trp Ser Arg Pro Gln Gly Trp
            500                 505                 510

Tyr Asn His Ser Gly Lys Glx
        515

<210> SEQ ID NO 7
<211> LENGTH: 11
<212> TYPE: RNA
<213> ORGANISM: Artificial sequence
<220> FEATURE:
<223> OTHER INFORMATION: synthetic

<400> SEQUENCE: 7
ggaauuggag c                                                            11

<210> SEQ ID NO 8
<211> LENGTH: 11
<212> TYPE: RNA
<213> ORGANISM: Artificial sequence
<220> FEATURE:
<223> OTHER INFORMATION: antisense sequence

<400> SEQUENCE: 8
gcuccaauuc c                                                            11

<210> SEQ ID NO 9
<211> LENGTH: 11
<212> TYPE: DNA
<213> ORGANISM: Artificial sequence
<220> FEATURE:
```

-continued

```
<223> OTHER INFORMATION: antisense sequence

<400> SEQUENCE: 9
gctccaattc c                                                           11

<210> SEQ ID NO 10
<211> LENGTH: 17
<212> TYPE: PRT
<213> ORGANISM: Artificial sequence
<220> FEATURE:
<223> OTHER INFORMATION: DEVD linker sequence

<400> SEQUENCE: 10

Gly Ser Gly Ser Gly Ser Asp Glu Val Asp Gly Gly Ser Gly Ser Gly
1               5                   10                  15

Ser
```